United States Patent [19]

Shiota et al.

[11] Patent Number: 5,574,061
[45] Date of Patent: Nov. 12, 1996

[54] BENZOPYRAN DERIVATIVE, PROCESS FOR PRODUCING THE SAME AND PHARMACEUTICAL COMPOSITION CONTAINING THE SAME

[75] Inventors: Tatsuki Shiota; Takumi Takeyasu, both of Hino; Kenichiro Kataoka, Tokyo; Tsutomu Mochizuki, Hino; Hirofumi Tanabe, Hino; Mikio Ota, Hino; Hisao Yamaguchi, Hino, Japan

[73] Assignee: Teijin Limited, Osaka, Japan

[21] Appl. No.: 216,779

[22] Filed: Mar. 23, 1994

Related U.S. Application Data

[63] Continuation of Ser. No. 966,166, filed as PCT/JP91/00999, Jul. 25, 1991, published as WO92/01681, Feb. 6, 1992, abandoned.

[30] Foreign Application Priority Data

| Jul. 25, 1990 | [JP] | Japan | 2-194857 |
| Oct. 22, 1990 | [JP] | Japan | 2-281863 |
| Apr. 11, 1991 | [JP] | Japan | 3-105180 |

[51] Int. Cl.⁶ .................... A61K 31/35; C07D 311/04
[52] U.S. Cl. ............................ 514/456; 549/404
[58] Field of Search ..................... 549/404; 514/456

[56] References Cited

U.S. PATENT DOCUMENTS 4,716,175  12/1987  Hoeffle et al. .................... 514/357

FOREIGN PATENT DOCUMENTS 0293880  12/1988  European Pat. Off. .
0297610  1/1989  European Pat. Off. .

OTHER PUBLICATIONS

Morrison & Boyd "Organic Chemistry" 3rd Ed. Allyn & Bacon, 1976, pp. 591 and 1044.

*Primary Examiner*—Philip Tucker
*Assistant Examiner*—Catherine Kilby Scalzo
*Attorney, Agent, or Firm*—Sughrue, Mion, Zinn, Macpeak & Seas

[57] ABSTRACT

A benzopyran derivative represented by the formula (I) or its pharmaceutically acceptable salt:

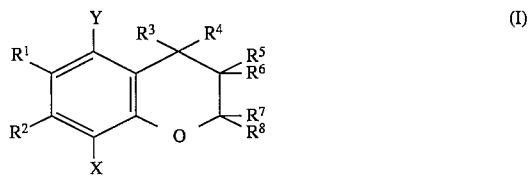

wherein either one of X and Y stands for the following formula

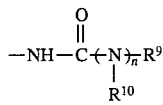

and the other one of X and Y and $R^1$–$R^{10}$ stand for various substituents,
and ACAT inhibitor, anti-hyperlipidemia agent and anti-atherosclerosis agent compositions containing the same as an active ingredient.

15 Claims, No Drawings

BENZOPYRAN DERIVATIVE, PROCESS FOR PRODUCING THE SAME AND PHARMACEUTICAL COMPOSITION CONTAINING THE SAME

This is a Continuation of application Ser. No. 07/966,166, filed as PCT/JP91/00999, Jul. 25, 1991, published as WO92/01681, Feb. 6, 1992, now abandoned.

TECHNICAL FIELD

The present invention relates to a novel benzopyran derivative, a process for producing the same and a pharmaceutical composition containing the same as an active ingredient. More specifically, it relates to a benzopyran derivative having on its aromatic ring an acylamino group or a substituted urea group and a pharmaceutically acceptable acid adduct thereof, a process for producing the same and a pharmaceutical composition containing the same as an active ingredient for treating hyperlipidemia and atherosclerosis based on an ACAT inhibitory activity.

BACKGROUND ART

As is well known, atherosclerosis is a very important factor causative of various cardiovascular disorders, and extensive and intensive studies have been conducted with a view to suppression of the progress of atherosclerosis or regression of atherosclerosis. In particular, the efficacy of a drug for lowering cholesterol in the serum or arterial wall is recognized. However, an ideal drug having a significant clinical effect and less liable to occurrence of an adverse effect has not been realized in the art.

In recent years, it has become apparent that the accumulation of a cholesterol ester in the arterial wall is an important factor causative of the progress of atherosclerosis. Therefore, lowering the cholesterol level in the blood is useful for suppression of the progress of atherosclerosis and regression of atherosclerosis.

Cholesterol in foods is esterified in tunica mucosa intestini tenuis and then incorporated as chylomicron in the blood. It is known that Acyl-CoA: Cholesterol Acyltransferase (ACAT) plays an important role in the formation of a cholesterol ester in the tunica mucosa intestini tenuis or arterial wall. Therefore, it is considered that the inhibition of ACAT in the tunica mucosa intestini tenuis to prevent the esterification prevents the absorption of the cholesterol, which contributes to lowering the cholesterol level in the blood.

In the arterial wall, the cholesterol is accumulated as a cholesterol ester. Therefore, it is expected that the inhibition of ACAT in the arterial wall can effectively prevent the accumulation of the cholesterol ester.

Thus, an ACAT inhibitor is considered likely to become a drug useful for treating hyperlipidemia and atherosclerosis through the prevention of the cholesterol absorption in intestinum tenue and the accumulation of the cholesterol in the arterial wall.

For example, urea derivatives (see, for example, J. Med. Chem., vol. 29, 1131 (1986) and Japanese Unexamined Patent Publication (Kokai) Nos. 63-316761 and 1-93569) and amide derivatives (see, for example, Japanese Examined Patent Publication (Kokoku) No. 63-54718 and Japanese Unexamined Patent Publication (Kokai) No. 63-253060) have hitherto been reported as such an ACAT enzyme inhibitor. These compounds are different from the compounds of the present invention in their structures.

On the other hand, U.S. Pat. No. 4,415,741 describes a benzopyran derivative. However, no specific disclosure of the compounds of the present invention is found therein, and up to now, it has been unknown that benzopyran derivatives have an ACAT inhibitory activity. 6-Acylaminochromanones with anti-hyperlipidemic activity (see, for example, Japanese Examined Patent Publication (Kokoku) Nos. 60-15626 and 60-35346) are known in the art. These compounds, however, are inferior to the compounds of the present invention in the activity thereof, and it was unknown that they have an ACAT inhibitory activity. Further, chromanones having a urea group on their aromatic ring (see J. Med. Chem., vol. 13, 584 (1970)) and 8-acylaminobenzopyrans having a leukotriene antagonism (see, for example, Japanese Unexamined Patent Publication (Kokai) Nos. 61-50977, 61-126061, 61-143371 and 62-230760 and J. Med. Chem., vol. 31, 84 (1988)) and 8-acylaminochromanones having a local anesthetic action (see Khim. Getrotsikl. Soedin., 320 (1987)) are also known in the art. However, it was unknown that they have an anti-hyperlipidemia activity and an ACAT inhibitory activity.

DISCLOSURE OF THE INVENTION

Accordingly, an object of the present invention is to provide a novel benzopyran derivative having an ACAT enzyme inhibitory activity and capable of exhibiting an excellent therapeutic effect through lowering the level of cholesterol in the arterial wall, a process for producing the same and a drug containing the same.

Other objects and advantages of the present invention will become apparent from the following description.

In accordance with the present invention, there is provided a benzopyran derivative represented by the formula (I) or pharmaceutically acceptable salt thereof:

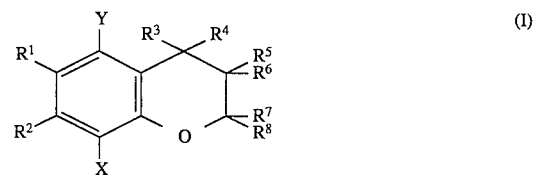

wherein either one of X and Y stands for the formula:

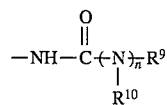

and the remainder stands for the same substituent as $R^1$ and $R^2$;

$R^1$ and $R^2$ each independently stand for a hydrogen atom, a halogen atom, an unsubstituted or substituted $C_1$–$C_6$ lower alkyl group, an unsubstituted or substituted $C_1$–$C_6$ lower alkoxy group, a hydroxyl group, a nitro group, a cyano group, a $C_1$–$C_6$ lower alkylamino group, a $C_1$–$C_{12}$ lower alkylamino group, a $C_1$–$C_7$ lower alkyloxycarbonyl group, a carboxyl group, a $C_1$–$C_7$ lower acyl group or a $C_1$–$C_{12}$ lower acyloxy group;

$R^3$ to $R^8$ each independently stand for a hydrogen atom or an unsubstituted or substituted $C_1$–$C_3$ lower alkyl group, provided that $R^3$ and $R^4$ may be combined with each other to represent an oxygen atom, $R^5$ and $R^7$ may be combined with each other to represent a carbon-carbon bond and $R^7$ and $R^8$ may be combined with each other to form a $C_5-C_7$ carbon ring;

$R^9$ stands for a substituted $C_6-C_{20}$ aryl group, an unsubstituted $C_5-C_{20}$ cycloalkyl or cycloalkenyl group or a substituted $C_5-C_{20}$ cycloalkyl or cycloalkenyl group having a substituent at a position other than the 1-position, or a group represented by the formula:

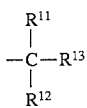

wherein $R^{11}$ and $R^{12}$ each independently stand for a hydrogen atom or an unsubstituted or substituted $C_1-C_6$ lower alkyl group, provided that $R^{11}$ and $R^{12}$ may be combined with each other to form a $C_3-C_7$ carbon ring; and $R^{13}$ stands for an unsubstituted or substituted $C_5-C_{19}$ chain or cyclic alkyl or alkenyl group, an unsubstituted or substituted $C_6-C_{19}$ aryl group, an unsubstituted or substituted $C_6-C_{19}$ arylalkyl group or a group represented by the formula unsubstituted or substituted $C_6-C_{19}$ arylalkyl group or a group represented by the formula

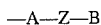

wherein A stands for a $C_1-C_{12}$ alkyl group, Z stands for an oxygen atom, a sulfur atom or a group represented by the formula

wherein $R^{14}$ stands for a hydrogen atom, a $C_1-C_6$ lower alkyl group or a $C_1-C_6$ lower acyl group, or may be combined with B to form a cyclic amine, provided that the cyclic amine may be formed through an oxygen atom, a sulfur atom or a nitrogen atom which may be substituted with a $C_1-C_6$ lower alkyl group or a $C_6-C_{19}$ arylalkyl group; and B stands for an unsubstituted or substituted $C_1-C_{19}$ alkyl group, an unsubstituted or substituted $C_6-C_{19}$ aryl group or an unsubstituted or substituted $C_6-C_{19}$ arylalkyl group;

$R^{10}$ stands for a hydrogen atom or a $C_1-C_6$ lower alkyl group; and n is 0 or 1.

In accordance with the present invention, there is also provided a process for producing a benzopyran derivative represented by the formula (I-a) or its pharmaceutically acceptable salt:

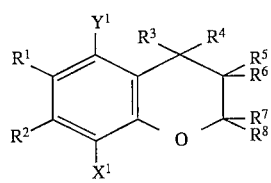

(I-a)

wherein either one of $X^1$ and $Y^1$ stands for the formula:

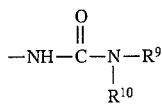

and the remainder stands for the same substituent as $R^1$ and $R^2$;

$R^1$ and $R^2$ each independently stand for a hydrogen atom, a halogen atom, an unsubstituted or substituted $C_1-C_6$ lower alkyl group, an unsubstituted or substituted $C_1-C_6$ lower alkoxy group, a hydroxyl group, a nitro group, a cyano group, a $C_1-C_6$ lower acylamino group, a $C_1-C_{12}$ lower alkylamino group, a $C_1-C_7$ lower alkyloxycarbonyl group, a carboxyl group, a $C_1-C_7$ lower acyl group or a $C_1-C_7$ lower acyloxy group;

$R^3$ to $R^8$ each independently stand for a hydrogen atom or an unsubstituted or substituted $C_1-C_3$ lower alkyl group, provided that $R^3$ and $R^4$ may be combined with each other to represent an oxygen atom, $R^5$ and $R^7$ may be combined with each other to represent a carbon-carbon bond and $R^7$ and $R^8$ may be combined with each other to form a $C_5-C_7$ carbon ring;

$R^9$ stands for a $C_6-C_{20}$ aryl group, an unsubstituted $C_5-C_{20}$ cycloalkyl or cycloalkenyl group or a substituted $C_5-C_{20}$ cycloalkyl or cycloalkenyl group having a substituent at a position other than the 1-position, or a group represented by the formula:

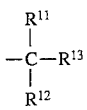

wherein $R^{11}$ and $R^{12}$ each independently stand for a hydrogen atom or an unsubstituted or substituted $C_1-C_6$ lower alkyl group, provided that $R^{11}$ and $R^{12}$ may be combined with each other to form a $C_3-C_7$ carbon ring; and $R^{13}$ stands for an unsubstituted or substituted $C_5-C_{19}$ chain or cyclic alkyl or alkenyl group, an unsubstituted or substituted $C_6-C_{19}$ aryl group, an unsubstituted or substituted $C_6-C_{19}$ arylalkyl group or a group represented by the formula:

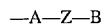

wherein A stands for a $C_1-C_{12}$ alkyl group, Z stands for an oxygen atom, a sulfur atom or a group represented by the formula:

wherein $R^{14}$ stands for a hydrogen atom, a $C_1-C_6$ lower alkyl group or a $C_1-C_6$ lower acyl group, or may be combined with B to form a cyclic amine, provided that the cyclic amine may be formed through an oxygen atom, a sulfur atom or a nitrogen atom which may be substituted with a $C_1-C_6$ lower alkyl group or a $C_6-C_{19}$ arylalkyl group; and B stands for an unsubstituted or substituted $C_1-C_{19}$ alkyl group, an unsubstituted or substituted $C_6-C_{19}$ aryl group or an unsubstituted or substituted $C_6-C_{19}$ arylalkyl group; and $R^{10}$ stands for a hydrogen atom or a $C_1$-$C_6$ lower alkyl group, comprising reacting a compound represented by the formula (II-a):

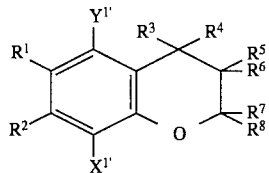
(II-a)

wherein $X^{1'}$ and $Y^{1'}$ are respectively the same as X and Y, except that any one of $X^{1'}$ and $Y^{1'}$ stands for —N═C═O and $R^1$ to $R^8$ are as defined above, with a compound represented by the formula:

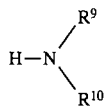

wherein $R^9$ and $R^{10}$ are as defined above.

In accordance with the present invention, there is further provided a process for producing a benzopyran derivative represented by the formula (I-b) and its pharmaceutically acceptable salt:

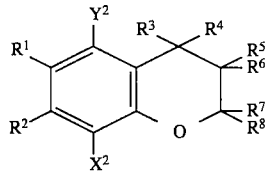
(I-b)

wherein either one of $X^2$ and $Y^2$ stands for the formula:

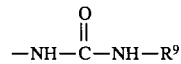

and the remainder stands for the same substituent as $R^1$ and $R^2$;

$R^1$ and $R^2$ each independently stand for a hydrogen atom, a halogen atom, an unsubstituted or substituted $C_1$-$C_6$ lower alkyl group, an unsubstituted or substituted $C_1$-$C_6$ lower alkoxy group, a hydroxyl group, a nitro group, a cyano group, a $C_1$-$C_6$ lower acylamino group, a $C_1$-$C_{12}$ lower alkylamino group, a $C_1$-$C_7$ lower alkyloxycarbonyl group, a carboxyl group, a $C_1$-$C_7$ lower acyl group or a $C_1$-$C_7$ lower acyloxy group;

$R^3$ to $R^8$ each independently stand for a hydrogen atom or an unsubstituted or substituted $C_1$-$C_3$ lower alkyl group, provided that $R^3$ and $R^4$ may be combined with each other to represent an oxygen atom, $R^5$ and $R^7$ may be combined with each other to represent a carbon-carbon bond and $R^7$ and $R^8$ may be combined with each other to form a $C_5$-$C_7$ carbon ring;

$R^9$ stands for a substituted $C_6$-$C_{20}$ aryl group, an unsubstituted $C_5$-$C_{20}$ cycloalkyl or cycloalkenyl group or a substituted $C_5$-$C_{20}$ cycloalkyl or cycloalkenyl group having a substituent at a position other than the 1-position, or a group represented by the formula:

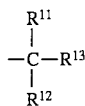

wherein $R^{11}$ and $R^{12}$ each independently stand for a hydrogen atom or an unsubstituted or substituted $C_1$-$C_6$ lower alkyl group, provided that $R^{11}$ and $R^{12}$ may be combined with each other to form a $C_3$-$C_7$ carbon ring; and $R^{13}$ stands for an unsubstituted or substituted $C_5$-$C_{19}$ chain or cyclic alkyl or alkenyl group, an unsubstituted or substituted $C_6$-$C_{19}$ aryl group, an unsubstituted or substituted $C_6$-$C_{19}$ arylalkyl group or a group represented by the formula:

—A—Z—B wherein A stands for a $C_1$-$C_{12}$ alkyl group and Z stands for an oxygen atom, a sulfur atom or a group represented by the formula:

wherein $R^{14}$ stands for a hydrogen atom, a $C_1$-$C_6$ lower alkyl group or a $C_1$-$C_6$ lower acyl group, or may be combined with B to form a cyclic amine wherein $R_{14}$ represents a $C_1$-$C_{19}$ alkyl group substituted through an oxygen atom, a sulfur atom or a nitrogen atom which may be substituted with a $C_1$-$C_6$ lower alkyl group or a $C_6$-$C_{19}$ arylalkyl group, or an unsubstituted or substituted $C_6$-$C_{19}$ alkyl group or an unsubstituted or substituted $C_6$-$C_{19}$ arylalkyl group; and $R^{10}$ stands for a hydrogen atom or a $C_1$-$C_6$ lower alkyl group, comprising reacting a compound represented by the formula (II-b):

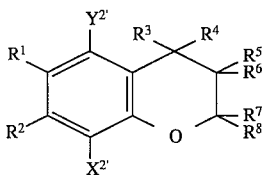
(II-b)

wherein $X^{2'}$ and $Y^{2'}$ are respectively the same as X and Y, except that any one of $X^{2'}$ and $Y^{2'}$ stands for —$NH_2$ and $R^1$ to $R^8$ are as defined above, with a compound represented by the formula:

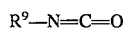

wherein $R^9$ is as defined above.

In accordance with the present invention, there is further provided a process for producing a benzopyran derivative represented by the formula (I-c) or its pharmaceutically acceptable salt:

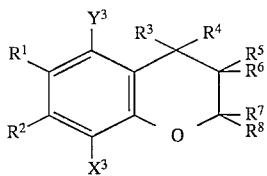 (I-c)

wherein either one of $X^3$ and $Y^3$ stands for the formula:

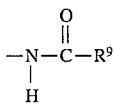

and the remainder stands for the same substituent as $R^1$ and $R^2$;

$R^1$ and $R^2$ each independently stand for a hydrogen atom, a halogen atom, an unsubstituted or substituted $C_1$–$C_6$ lower alkyl group, an unsubstituted or substituted $C_1$–$C_6$ lower alkoxy group, a hydroxyl group, a nitro group, a cyano group, a $C_1$–$C_6$ lower acylamino group, a $C_1$–$C_{12}$ lower alkylamino group, a $C_1$–$C_7$ lower alkyloxycarbonyl group, a carboxyl group, a $C_1$–$C_7$ lower acyl group or a $C_1$–$C_7$ lower acyloxy group;

$R^3$ to $R^8$ each independently stand for a hydrogen atom or an unsubstituted or substituted $C_1$–$C_3$ lower alkyl group, provided that $R^3$ and $R^4$ may be combined with each other to represent an oxygen atom, $R^5$ and $R^7$ may be combined with each other to represent a carbon-carbon bond and $R^7$ and $R^8$ may be combined with each other to form a $C_5$–$C_7$ carbon ring;

$R^9$ stands for a substituted $C_6$–$C_{20}$ aryl group, an unsubstituted $C_5$–$C_{20}$ cycloalkyl or cycloalkenyl group or a substituted $C_5$–$C_{20}$ cycloalkyl or cycloalkenyl group having a substituent at a position other than the 1-position, or a group represented by the formula:

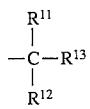

wherein $R^{11}$ and $R^{12}$ each independently stand for a hydrogen atom or an unsubstituted or substituted $C_1$–$C_6$ lower alkyl group, provided that $R^{11}$ and $R^{12}$ may be combined with each other to form a $C_3$–$C_7$ carbon ring; and $R^{13}$ stands for an unsubstituted or substituted $C_5$–$C_{19}$ chain or cyclic alkyl or alkenyl group, an unsubstituted or substituted $C_6$–$C_{19}$ aryl group, an unsubstituted or substituted $C_6$–$C_{19}$ arylalkyl group or a group represented by the formula:

—A—Z—B wherein A stands for a $C_1$–$C_{12}$ alkyl group, Z stands for an oxygen atom, a sulfur atom or a group represented by the formula:

wherein $R^{14}$ stands for a hydrogen atom, a $C_1$–$C_6$ lower alkyl group or a $C_1$–$C_6$ lower acyl group, or may be combined with B to form a cyclic amine, provided that the cyclic amine may be formed through an oxygen atom, a sulfur atom or a nitrogen atom which may be substituted with a $C_1$–$C_6$ lower alkyl group or a $C_6$–$C_{19}$ arylalkyl group; and B stands for an unsubstituted or substituted $C_1$–$C_{19}$ alkyl group, an unsubstituted or substituted $C_6$–$C_{19}$ aryl group or an unsubstituted or substituted $C_6$–$C_{19}$ arylalkyl group; and $R^{10}$ stands for a hydrogen atom or a $C_1$–$C_6$ lower alkyl group, comprising reacting a compound represented by the formula (II-c):

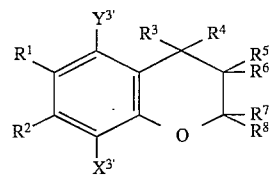 (II-c)

wherein $X^{3'}$ and $Y^{3'}$ are respectively the same as X and Y, except that any one of $X^{3'}$ and $Y^{3'}$ stands for —$NH_2$ and $R^1$ to $R^8$ are as defined above, with a compound represented by the formula:

$R^9COOH$ wherein $R^9$ is as defined above, or its reactive derivatives.

In accordance with the present invention, there are further provided pharmaceutical compositions containing the same benzopyran derivatives as described above, and the pharmaceutically acceptable salts thereof for treating hyperlipidemia and atherosclerosis based on the ACAT inhibitory activity.

BEST MODE FOR CARRYING OUT THE INVENTION

The benzopyran derivative represented by the formula (I) according to the present invention may be roughly classified into the compound having a substituted urea group on the aromatic ring thereof represented by the formula (I) wherein n is 1 and the compound having an acylamino group on the aromatic ring thereof represented by the formula (I) wherein n is 0. Further, each of these compounds is classified into chroman derivatives represented by the formula (I), wherein $R^3$ and $R^4$ each independently stand for a hydrogen atom or an unsubstituted or substituted $C_1$–$C_3$ lower alkyl group, and the pharmaceutically acceptable salt thereof; chromanone derivatives represented by the formula (I), wherein $R^3$ and $R^4$ are combined with each other to represent an oxygen atom and $R^5$ and $R^7$ are not combined with each other to represent a carbon-carbon bond, and the pharmaceutically acceptable salt thereof; and chromone derivatives represented by the formula (I), wherein $R^3$ and $R^4$ are combined with each other to represent an oxygen atom and $R^5$ and $R^7$ are combined with each other to represent a carbon-carbon bond.

Benzopyran derivatives of the first group according to the present invention are represented by the formula (I-a):

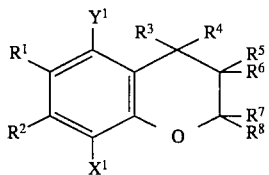 (I-a)

wherein either one of $X^1$ and $Y^1$ stands for the following formula:

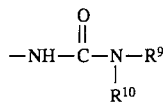

and the remainder stands for the same substituent as $R^1$ and $R^2$.

In the formula (I-a), $R^1$ and $R^2$ each independently stand for a hydrogen atom, a halogen atom, an unsubstituted or substituted $C_1$–$C_6$ lower alkyl group, an unsubstituted or substituted $C_1$–$C_6$ lower alkoxy group, a hydroxyl group, a nitro group, a cyano group, a $C_1$–$C_6$ lower acylamino group, a $C_1$–$C_{12}$ lower alkylamino group, a $C_1$–$C_7$ lower alkyloxycarbonyl group, a carboxyl group, a $C_1$–$C_7$ lower acyl group or a $C_1$–$C_7$ lower acyloxy group. Examples of the halogen atom include a fluorine atom, a chlorine atom and a bromine atom. The term "lower alkyl group" is intended to mean a $C_1$–$C_6$ chain (straight-chain or branched) or cyclic alkyl group, and preferred examples thereof include methyl, ethyl, propyl, isopropyl, butyl, isobutyl, sec-butyl, tert-butyl, pentyl, neopentyl, hexyl, cyclopropyl, cyclohexyl and cyclopropylmethyl. The term "lower alkoxy group" is intended to mean a group comprising the above-described $C_1$–$C_6$ lower alkyl group and an oxy group, and preferred examples thereof include methoxy, ethoxy, propoxy, butoxy, isobutoxy, tert-butoxy, pentyloxy, hexyloxy, cyclopropyloxy, cyclohexyloxy and cyclopropylmethoxy. The term "lower alkylamino group" is intended to mean a mono- or dialkylamino group comprising a $C_1$–$C_6$ lower alkyl group, which may be the same as or different from the above-described $C_1$–$C_6$ lower alkyl group, and an amino group, and preferred examples thereof include methylamino, ethylamino, dimethylamino, diethylamino and N-butyl-N-methylamino. The term "lower alkoxycarbonyl group" is intended to mean a group comprising the above-described $C_1$–$C_6$ lower alkoxy group and a carbonyl group, and preferred examples thereof include methoxycarbonyl, ethoxycarbonyl, propoxycarbonyl and tert-butoxycarbonyl. The term "lower acyl group" is intended to mean a group comprising the above-described $C_1$–$C_6$ lower alkyl group and a carbonyl group, and preferred examples thereof include acetyl, propionyl, butyryl and benzoyl. The term "lower acylamino group" is intended to mean a group comprising the above-described $C_1$–$C_7$ lower acyl group and an amino group, and preferred examples thereof include acetylamino, propionylamino and benzoylamino. The term "lower acyloxy group" is intended to mean a group comprising the above-described $C_1$–$C_7$ lower acyl group and an oxy group, and preferred examples thereof include acetoxy, propionyloxy, butyryloxy and benzoyloxy. Further, examples of the substituent of the substituted lower alkyl group or lower alkoxy group include a halogen atom, a hydroxyl group and an amino group. Examples of the substituted lower alkyl group etc. include a trifluoromethyl group.

In the formula (I-a), $R^3$ to $R^8$ each independently stand for a hydrogen atom or an unsubstituted or substituted $C_1$–$C_3$ lower alkyl group, provided that $R^3$ and $R^4$ may be combined with each other to represent an oxygen atom, $R^5$ and $R^7$ may be combined with each other to represent a carbon-carbon bond and $R^7$ and $R^8$ may be combined with each other to form a $C_5$–$C_7$ carbon ring. Preferred examples of the $C_1$–$C_3$ lower alkyl group include methyl, ethyl, propyl and isopropyl.

In the formula (I-a), $R^9$ stands for a substituted $C_6$–$C_{20}$ aryl group, an unsubstituted $C_5$–$C_{20}$ cycloalkyl or cycloalkenyl group or a substituted $C_5$–$C_{20}$ cycloalkyl or cycloalkenyl group having a substituent at a position other than the 1-position, or a group represented by the formula:

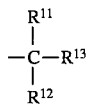

The term "substituted aryl group" is intended to mean an aromatic hydrocarbon group substituted with a halogen atom, a $C_1$–$C_{14}$ chain (straight-chain or branched) or cyclic alkyl group, a $C_1$–$C_{14}$ alkoxy group, a $C_1$–$C_{14}$ acylamino group, a $C_1$–$C_{14}$ mono- or dialkylamino group, a $C_1$–$C_{14}$ alkyloxycarbonyl group, a $C_1$–$C_{14}$ acyl group or a $C_1$–$C_{14}$ acyloxy group, and preferred examples thereof include p-fluorophenyl, p-decylphenyl, p-methoxyphenyl, p-isohexyloxyphenyl, p-decyloxyphenyl, p-butyrylaminophenyl, p-(N-butyl-N-methylaminophenyl), p-valeryloxyphenyl and m-heptanoylphenyl groups. Specific preferred examples of the unsubstituted cycloalkyl or cycloalkenyl group or the cycloalkyl or cycloalkenyl group having a substituent at a position other than the 1-position include cyclopentyl, cyclohexyl, cycloheptyl, 1-cyclohexene-1-yl, 4-hexylcyclohexyl and 4-decyloxycyclohexyl.

$R^{11}$ and $R^{12}$ each independently stand for a hydrogen atom or an unsubstituted or substituted $C_1$–$C_6$ lower alkyl group or may be combined with each other to form a $C_3$–$C_7$ carbon ring. The lower alkyl group has the same meaning as the lower alkyl group defined above in connection with the $R^1$, and preferred examples thereof are also the same as those of the lower alkyl group in the $R^1$. $R^{13}$ stands for an unsubstituted or substituted $C_5$–$C_{19}$ chain or cyclic alkyl or alkenyl group, an unsubstituted or substituted $C_6$–$C_{19}$ aryl group or an unsubstituted or substituted $C_6$–$C_{19}$ arylalkyl group. When the $R^{13}$ stands for a $C_5$–$C_{19}$ alkyl group, preferred examples of the $R^9$ include hexyl, isohexyl, octyl, undecyl, dodecyl, tridecyl, pentadecyl, hexadecyl, heptadecyl, nonadecyl, icosyl, 1,1-dimethylheptyl, 1,1-dimethylundecyl, 1,1,12,12-tetramethyltridecyl, 1-methyltridecyl, 1-decylcyclohexyl, 1-decylcyclopentyl, 1-dodecylcyclopropyl, 1-cyclohexyl-1-methylethyl and 1-ethyloctyl. When the $R^{13}$ stands for a $C_5$–$C_{19}$ alkenyl group, preferred examples of the $R^9$ include hexenyl, 8-tridecenyl, 8-heptadecenyl, 9-octadecenyl, 8,11-heptadecadienyl, 1,1-dimethyl-8-nonenyl and cyclohexenylmethyl. When the $R^{13}$ stands for a $C_5$–$C_{19}$ aryl group, preferred examples of the $R^9$ include benzyl, 1-phenylcyclopentyl, 1-phenylethyl and 1-methyl-1-(2-pyridyl)-ethyl. When the $R^{13}$ stands for a $C_5$–$C_{19}$ arylalkyl group, preferred examples of the $R^9$ include 2-phenylethyl, 8-phenyloctyl, 1,1-dimethyl-11-phenylundecyl, 1-benzylcyclopentyl, (1-phenylcyclopentyl)methyl, 1,1-dimethyl-4-(1-methyl-1,2,3,4-tetrahydroquinoline-6-yl) butyl, 1,1-dimethyl-7-pyridylheptyl and 2,2-diphenylethyl. Further, $R^{13}$ stands for a group represented by the formula —A—Z—B wherein A stands for a $C_1$–$C_{12}$ alkyl group; Z stands for an oxygen atom, a sulfur atom or a group represented by the formula:

wherein $R^{14}$ stands for a hydrogen atom, a $C_1$–$C_6$ lower alkyl group or a $C_1$–$C_6$ lower acyl group, or may be combined with B to form a cyclic amine, provided that the cyclic amine may be formed through an oxygen atom, a sulfur atom or a nitrogen atom which may be substituted with a $C_1$–$C_6$ lower alkyl group or a $C_6$–$C_{19}$ arylalkyl group; and B stands for an unsubstituted or substituted $C_1$–$C_{19}$ alkyl group, an unsubstituted or substituted $C_6$–$C_{19}$ aryl group or an unsubstituted or substituted $C_6$–$C_{19}$ arylalkyl group. The lower alkyl group or lower acyl group in the $R^{14}$ has the same meaning as the lower alkyl group or lower acyl group defined above in connection with the $R^1$, and specific preferred examples thereof are also the same as those of the lower alkyl group in the $R^1$. Preferred examples of the case where $R^{14}$ combines with B to form a cyclic amine include 1-pyrrolidinyl, piperidino, morpholino, thiomorpholino, 4-methyl-1-piperazinyl and 4-benzyl-1-piperazinyl. The alkyl group in the B has the same meaning as the alkyl group defined above in connection with the $R^1$ and $R^{13}$, and preferred examples thereof are also the same as those of the alkyl group in the $R^1$ and $R^{13}$. The aryl group and arylalkyl group in the B have the same meaning as the aryl group and arylalkyl group defined above in connection with the $R^{13}$, and preferred examples thereof are also the same as those of the aryl group and arylalkyl group in the $R^{13}$. When the $R^{13}$ stands for a group represented by the formula —A—Z—B, preferred examples of the $R^9$ include 6-isobutoxyhexyl, 6-p-chlorophenoxyhexyl, 5-p-dimethylaminophenoxypentyl, 5-isohexyloxy-1,1-dimethylpentyl, 7-isohexyloxy-1,1-dimethylheptyl, 7-isobutoxy-1,1-dimethylheptyl, 7-neopentyloxy-1,1-dimethylheptyl, 5-p-chlorophenoxy-1,1-dimethylpentyl, 6-p-chlorophenoxy-1,1-dimethylhexyl, 7-p-chlorophenoxy-1,1-dimethylheptyl, 1,1-dimethyl-7-p-tolyloxyheptyl, 5-(p-tert-butylphenoxyl)pentyl, 1,1-dimethyl-6-p-dimethylaminophenoxyhexyl, 1,1-dimethyl-7-p-dimethylaminophenoxyheptyl, 7-isopropylamino-1,1-dimethylheptyl, 7-benzylamino-1,1-dimethylheptyl, 7-(N-benzyl-N-methylamino)-1,1-dimethylheptyl, 7-(N-p-chlorobenzyl-N-methylamino)-1,1-dimethylheptyl, 7-(N-p-chlorophenyl-N-methylamino)-1,1-dimethylheptyl, 1,1-dimethyl-7-piperidinoheptyl, 1,1-dimethyl-7-(4-methyl-1-piperazinyl)heptyl, 7-(4-benzyl-1-piperazinyl)-1,1-dimethylheptyl, 5-(4-benzyl-1-piperazinyl)-1,1-dimethylpentyl and 6-(p-chlorophenylthio)-1,1-dimethylhexyl. Further, each group represented by the $R^{13}$ may be substituted with a single substituent or plural substituents selected from a halogen atom, a lower alkyl group, a lower alkoxy group, a hydroxyl group, a nitro group, a cyano group, a lower acylamino group, a lower alkylamino group, a lower alkyloxycarbonyl group, a carboxyl group, a lower acyl group and a lower acyloxycarbonyl group. These substituents have the same meaning as the substituents defined above in connection with the $R^1$, and preferred examples thereof are also the same as those of the substituents in the $R^1$. Preferred examples of the $R^9$ including the $R^{13}$ substituted with the above-described substituents include 10-ethoxycarbonyldecyl, 2-(p-nitrophenyl)ethyl, 7-p-chlorophenyl-1,1-dimethylheptyl, 4-p-isobutylphenyl-1,1-dimethylbutyl, 1-(3-benzoylpropyl)cyclopentyl, 4-p-diethylaminophenyl-1,1-dimethylbutyl, 6-p-ethoxyphenyl-1,1-dimethylhexyl, (1-m-cyanophenylcyclopentyl)methyl, (1-p-dimethylaminophenylcyclopentyl)methyl and (1-p-methoxyphenylcyclopentyl)methyl.

The $R^{10}$ in the formula (I-a) stands for a hydrogen atom or a $C_1$–$C_8$ lower alkyl group. The lower alkyl group has the same meaning as the lower alkyl group defined above in connection with the $R^1$, and preferred examples thereof are also the same as those of the lower alkyl group in the $R^1$.

This compound is produced by reacting a compound (benzopyranyl isocyanate) represented by the formula (II-a):

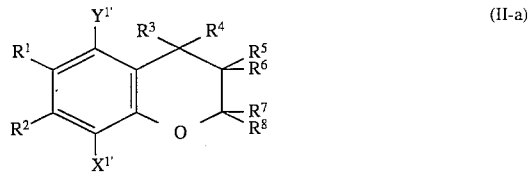

wherein $X^{1'}$ and $Y^{1'}$ are respectively the same as X and Y, except that any one of $X^{1'}$ and $Y^{1'}$ stands for —N=C=O and $R^1$ to $R^8$ are as defined above, with an amine compound represented by the formula:

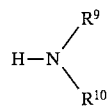

wherein $R^9$ and $R^{10}$ are as defined above.

The benzopyranyl isocyanate represented by the formula (II-a) can be produced by a conventional process. For example, it can be produced by subjecting a corresponding carboxylic acid amide to a Hofmann degradation, subjecting a carboxylic acid azide to a thermal decomposition reaction or reacting the corresponding amine with a phosgene or its homologous reagent.

The above-described amine compound can be produced by a conventional method.

The process provided by the present invention can be practiced by reacting one equivalent of benzopyranyl isocyanate represented by the formula (II-a) with 0.2 to 5 equivalents of the above-described amine compound in the absence or presence of a solvent. The reaction temperature is in the range of from –20° to 150° C., preferably in the range of from room temperature to 100° C., and the reaction time is usually 72 hrs or less. Examples of the reaction solvent include halogenated hydrocarbons such as dichloromethane and chloroform, aromatic hydrocarbons such as benzene and toluene, ethers such as diethyl ether and tetrahydrofuran and aprotic polar solvents such as ethyl acetate, dimethylformaldehyde and dimethylsulfoxide.

After the completion of the reaction, the reaction mixture may be subjected to conventional separation and purification procedure, that is, extraction, recrystallization, chromatography, etc. to isolate an intended benzopyran derivative represented by the formula (I-a). Further, the product can be converted to a pharmaceutically acceptable salt by a conventional method.

The second benzopyran derivatives according to the present invention are represented by the formula (I-b):

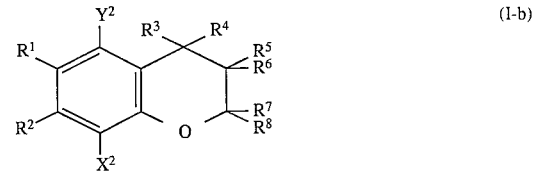

wherein either one of $X^2$ and $Y^2$ stands for the following formula

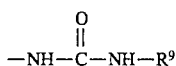

and the remainder stands for the same substituent as $R^1$ and $R^2$;

$R^1$ and $R^2$ each independently stand for a hydrogen atom, a halogen atom, an unsubstituted or substituted $C_1$–$C_6$ lower alkyl group, an unsubstituted or substituted $C_1$–$C_6$ lower alkoxy group, a hydroxyl group, a nitro group, a cyano group, a $C_1$–$C_6$ lower acylamino group, a $C_1$–$C_{12}$ lower alkylamino group, a $C_1$–$C_7$ lower alkyloxycarbonyl group, a carboxyl group, a $C_1$–$C_7$ lower acyl group or a $C_1$–$C_7$ lower acyloxy group;

$R^3$ to $R^8$ each independently stand for a hydrogen atom or an unsubstituted or substituted $C_1$–$C_3$ lower alkyl group, provided that $R^3$ and $R^4$ may be combined with each other to represent an oxygen atom, $R^5$ and $R^7$ may be combined with each other to represent a carbon-carbon bond and $R^7$ and $R^8$ may be combined with each other to form a $C_5$–$C_7$ carbon ring;

$R^9$ stands for a substituted $C_6$–$C_{20}$ aryl group, an unsubstituted $C_5$–$C_{20}$ cycloalkyl or cycloalkenyl group or a substituted $C_5$–$C_{20}$ cycloalkyl or cycloalkenyl group having a substituent at a position other than the 1-position, or a group represented by the formula:

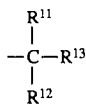

wherein $R^{11}$ and $R^{12}$ each independently stand for a hydrogen atom or an unsubstituted or substituted $C_1$–$C_6$ lower alkyl group, provided that $R^{11}$ and $R^{12}$ may be combined with each other to form a $C_3$–$C_7$ carbon ring; and $R^{13}$ stands for an unsubstituted or substituted $C_5$–$C_{19}$ chain or cyclic alkyl or alkenyl group, an unsubstituted or substituted $C_6$–$C_{19}$ aryl group, an unsubstituted or substituted $C_6$–$C_{19}$ arylalkyl group or a group represented by the formula:

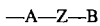

wherein A stands for a $C_1$–$C_{12}$ alkyl group and Z stands for an oxygen atom, a sulfur atom or a group represented by the formula:

wherein $R^{14}$ stands for a hydrogen atom, a $C_1$–$C_6$ lower alkyl group or a $C_1$–$C_6$ lower acyl group, or may be combined with B to form a cyclic amine, provided that the cyclic amine may be formed through an oxygen atom, a sulfur atom or a nitrogen atom which may be substituted with a $C_1$–$C_6$ lower alkyl group or a $C_6$–$C_{19}$ arylalkyl group; and B stands for an unsubstituted or substituted $C_1$–$C_{19}$ alkyl group, an unsubstituted or substituted $C_6$–$C_{19}$ aryl group or an unsubstituted or substituted $C_6$–$C_{19}$ arylalkyl group; and $R^{10}$ stands for a hydrogen atom or a $C_1$–$C_6$ lower alkyl group.

The substituents $R^1$ to $R^8$ in the formula (I-b) and the $R^9$ to $R^{14}$, A, Z and B associated with the $R^1$ to $R^8$ have the same meaning as respective substituents in the formula (I-b), and preferred examples thereof are also the same as those of the substituents in the formula (I-a).

These benzopyran derivatives are produced by reacting a compounds (i.e., benzopyranylamines) represented by the formula (II-b):

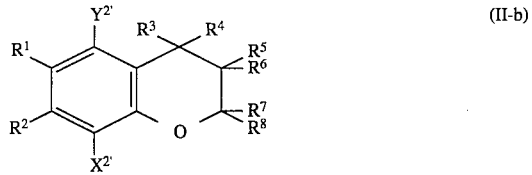

wherein $X^{2'}$ and $Y^{2'}$ are respectively the same as X and Y, except that any one of $X^{2'}$ and $Y^{2'}$ stands for —$NH_2$ and $R^1$ to $R^8$ are as defined above, with a compound represented by the formula:

wherein $R^9$ is as defined above.

The benzopyranylamines represented by the formula (II-b) can be produced by a conventional process. Further, the above-described isocyanate compound as well can be produced by a conventional process.

The process according to the present invention can be practiced by reacting one equivalent amount of a benzopyranylamine represented by the formula (II-b) with 0.2 to 5 equivalent amounts of the above-described isocyanate in the absence or presence of a solvent. The reaction temperature is in the range of from –20° C. to 150° C., preferably in the range of from room temperature to 100° C., and the reaction time is usually 72 hrs or less. Examples of the reaction solvent include halogenated hydrocarbons such as dichloromethane and chloroform, aromatic hydrocarbons such as benzene and toluene, ethers such as diethyl ether and tetrahydrofuran and aprotic polar solvents such as ethyl acetate, dimethylformaldehyde and dimethylsulfoxide.

After the completion of the reaction, the reaction mixture may be subjected to conventional separation and purification procedure, that is, extraction, recrystallization, chromatography, etc. to isolate an intended benzopyran derivative represented by the formula (I-b). Further, the product can be converted to a pharmaceutically acceptable salt by a conventional method.

The third benzopyran derivative according to the present invention is represented by the formula (I-c):

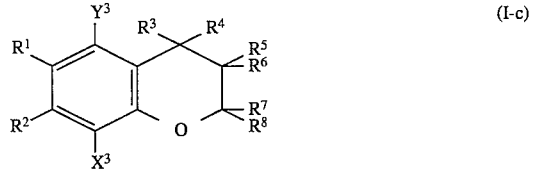

wherein either one of $X^3$ and $Y^3$ stands for the formula

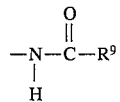

and the remainder stands for the same substituent as $R^1$ and $R^2$;

$R^1$ and $R^2$ each independently stand for a hydrogen atom, a halogen atom, an unsubstituted or substituted $C_1$–$C_6$ lower alkyl group, an unsubstituted or substituted $C_1$–$C_6$ lower alkoxy group, a hydroxyl group, a nitro group, a cyano group, a $C_1$–$C_6$ lower acylamino group, a $C_1$–$C_{12}$ lower alkylamino group, a $C_1$–$C_7$ lower alkyloxycarbonyl group, a carboxyl group, a $C_1$–$C_7$ lower acyl group or a $C_1$–$C_7$ lower acyloxy group;

$R^3$ to $R^8$ each independently stand for a hydrogen atom or an unsubstituted or substituted $C_1$–$C_3$ lower alkyl group, provided that $R^3$ and $R^4$ may be combined with each other to represent an oxygen atom, $R^5$ and $R^7$ may be combined with each other to represent a carbon-carbon bond and $R^7$ and $R^8$ may be combined with each other to form a $C_5$–$C_7$ carbon ring;

$R^9$ stands for a substituted $C_6$–$C_{20}$ aryl group, an unsubstituted $C_5$–$C_{20}$ cycloalkyl or cycloalkenyl group or a substituted $C_5$–$C_{20}$ cycloalkyl or cycloalkenyl group having a substituent at a position other than the 1-position, or a group represented by the formula:

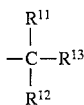

wherein $R^{11}$ and $R^{12}$ each independently stand for a hydrogen atom or an unsubstituted or substituted $C_1$–$C_6$ lower alkyl group, provided that $R^{11}$ and $R^{12}$ may be combined with each other to form a $C_3$–$C_7$ carbon ring; and $R^{13}$ stands for an unsubstituted or substituted $C_5$–$C_{19}$ chain or cyclic alkyl or alkenyl group, an unsubstituted or substituted $C_6$–$C_{19}$ aryl group, an unsubstituted or substituted $C_6$–$C_{19}$ arylalkyl group or a group represented by the formula:

wherein A stands for a $C_1$–$C_{12}$ alkyl group, Z stands for an oxygen atom, a sulfur atom or a group represented by the formula:

wherein $R^{14}$ stands for a hydrogen atom, a $C_1$–$C_6$ lower alkyl group or a $C_1$–$C_6$ lower acyl group, or may be combined with B to form a cyclic amine, provided that the cyclic amine may be formed through an oxygen atom, a sulfur atom or a nitrogen atom which may be substituted with a $C_1$–$C_6$ lower alkyl group or a $C_6$–$C_{19}$ arylalkyl group; and B stands for an unsubstituted or substituted $C_1$–$C_{19}$ alkyl group, an unsubstituted or substituted $C_6$–$C_{19}$ aryl group or an unsubstituted or substituted $C_6$–$C_{19}$ arylalkyl group;

The substituents $R^1$ to $R^8$ in the formula (I-c) and the $R^9$ to $R^{14}$, A, Z and B associated with the $R^1$ to $R^8$ have the same meaning as respective substituents in the formula (I-a), and preferred examples thereof are also the same as those of the substituents in the formula (I-a).

The above-described compounds (I-c) are produced by reacting a compound represented by the formula (II-c):

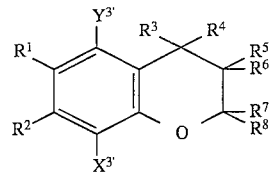

wherein $X^{3'}$ and $Y^{3'}$ are respectively the same as X and Y, except that any one of $X^{3'}$ and $Y^{3'}$ stands for —$NH_2$ and $R^1$ to $R^8$ are as defined above, with a compound represented by the formula:

wherein $R^9$ is as defined above, or its reactive derivatives.

As described above, the compounds represented by the formula (II-c) can be produced by a conventional process. Further, the above-described carboxylic acid compound or its reactive derivatives as well can be produced by a conventional process.

The process provided by the present invention can be practiced by reacting one equivalent of a benzopyranylamine represented by the formula (II-c) with 1 to 5 equivalents of the above-described carboxylic acid compound and a condensation agent, for example, 1 to 2 equivalents of dicyclohexylcarbodiimide and a basic amine compound, for example, 0.1 to 1.5 equivalents of triethylamine, pyridine or 4-dimethylaminopyridine, in the presence of a solvent.

The reaction temperature is in the range of from −20° C. to 150° C., preferably in the range of from room temperature to 100° C., and the reaction time is usually 72 hrs or less.

Alternatively, the process can be practiced by reacting one equivalent of a benzopyranylamine represented by the formula (II-c) with a reactive derivative of the above-described carboxylic acid, for example, 1 to 5 equivalents of a corresponding carboxylic acid chloride or acid anhydride, in the presence of a solvent.

The reaction temperature is in the range of from −20° C. to 150° C., preferably in the range of −10° C. to 100° C., and the reaction time is usually 72 hrs or less.

Examples of the reaction solvent include halogenated hydrocarbons such as dichloromethane and chloroform, aromatic hydrocarbons such as benzene and toluene, ethers such as diethyl ether and tetrahydrofuran and aprotic polar solvents such as ethyl acetate, dimethylformaldehyde and dimethylsulfoxide. In this case, it is possible to add 0.1 to 1.5 equivalents of a basic amine compound, for example, triethylamine, pyridine and 4-dimethylaminopyridine.

After the completion of the reaction, the reaction mixture may be subjected to conventional separation and purification procedure, that is, extraction, recrystallization, chromatography, etc., to isolate an intended benzopyran derivative represented by the formula (I-c).

According to the present invention, the compounds of the present invention may have a basic group in the molecule thereof. In this case, it may be in the form of an acid adduct. Examples of the acid include mineral acids such as hydrochloric acid, hydrobromic acid, sulfuric acid, phosphoric acid and carbonic acid and organic acids such as citric acid, malic acid, oxalic acid, tartaric acid, fumaric acid and methanesulfonic acid.

Specific preferred examples of the benzopyran derivatives represented by the formula (I) according to the present invention include compounds having substituents represented by the following Table. In the Tables, G stands for a group represented by the formula:

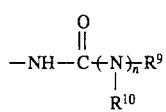
Further, when the structural formula representing the compounds of the present invention have an asymmetric carbon, the compounds of the present invention include all possible optical isomers.

| Compd. No. | $R^1$ | $R^2$ | X | Y | $R^3$ – $R^8$ | $R^9$ | $R^{10}$ |
|---|---|---|---|---|---|---|---|
| 101 | H | $OCH_3$ | G | H | $R^3 = CH_3, R^4 = CH_3$ | 4-methylphenyl with long alkyl chain | H |
| 102 | $\begin{array}{c} O \\ \parallel \\ -NCCH_3 \\ H \end{array}$ | $OCH_3$ | G | H | $R^3, R^4 = O$ | 4-methylphenyl-O-alkyl (isobutyl-terminated) | H |
| 103 | H | $CH_3$ | G | H | $R^3, R^4 = O, R^5, R^7 = $ bond | 4-methylphenyl with long alkyl chain | H |

| Compd. No. | $R^1$ | $R^2$ | X | Y | $R^3$ – $R^8$ | $R^{11}$ | $R^{12}$ | $R^{13}$ | $R^{10}$ |
|---|---|---|---|---|---|---|---|---|---|
| 104 | H | $OCH_3$ | G | H | $R^3 = CH_3, R^4 = CH_3$ | H | H | $-(CH_2)_{10}CH_3$ | H |
| 105 | $CH_3$ | H | G | H | $R^3 = CH_3, R^4 = CH_3$ | H | H | $-(CH_2)_{14}CH_3$ | H |
| 106 | H | $OCH_3$ | G | H | $R^3 = CH_3, R^4 = CH_3$ | H | H | $-(CH_2)_4CH_3$ | $-(CH_2)_5CH_3$ |
| 107 |  | $CH_3$ | G | H | $R^3 = CH_3, R^4 = CH_3$ | $CH_3$ | $CH_3$ | $-(CH_2)_9CH_3$ | H |
| 108 | H | $OCH_3$ | G | H | $R^3 = CH_3, R^4 = CH_3$ | H | H | 1-methylcyclopentyl with phenylalkyl | H |
| 109 | H | $CO_2CH_2CH_3$ | H | G | $R^7 = CH_3, R^8 = CH_3$ | H | H | phenylheptyl | H |
| 110 | H | $OCH_3$ | G | H | $R^3 = CH_3, R^4 = CH_3$ | H | H | 4-chlorophenoxyhexyl | H |

-continued

| No. | | | | | R³/R⁴ | | | | |
|---|---|---|---|---|---|---|---|---|---|
| 111 | H | OCH₃ | G | H | R³ = CH₃, R⁴ = CH₃ | H | 3-CN-phenyl-(1-methylcyclopentyl) | H | H |
| 112 | H | CH₃ | G | H | R³ = CH₃, R⁴ = CH₃ | H | 4-N(CH₃)₂-phenyl-(1-methylcyclopentyl) | H | H |
| 113 | H | CH₃ | G | H | R³, R⁴ = O | H | —(CH₂)₁₀CH₃ | H | H |
| 114 | OCH₃ | H | H | G | R³, R⁴ = O | H | —(CH₂)₁₄CH₃ | H | H |
| 115 | H | —CH(CH₃)₂ | G | H | R³, R⁴ = O | CH₃ | —(CH₂)₇CH₃ | CH₃ | H |
| 116 | Cl | CH₃ | G | CH₃ | R³, R⁴ = O | H | —(CH₂)₇CH=CH(CH₂)₇CH₃ | H | —(CH₂)₃CH₃ |
| 117 | H | OCH₃ | G | H | R³, R⁴ = O | H | tolyl | H | H |
| 118 | H | CH₃ | G | H | R³, R⁴ = O | H | phenyl-(1-methylcyclopentyl) | H | H |
| 119 | H | OCH₃ | G | H | R³, R⁴ = O | H | phenyl-(1-methylcyclopentyl) | H | CH₃ |
| 120 | —OC(O)CH₃ | H | H | G | R³, R⁴ = O | H | phenyl-(1-methylcyclopentyl) | H | CH₃ |

| | | | | | | |
|---|---|---|---|---|---|---|
| 121 | H | Cl | G | H | R³, R⁴ = O | *isobutoxyhexyl chain* | H |
| 122 | H | CH₃ | G | CH₃ | R³, R⁴ = O | *4-chlorophenoxyhexyl* | H |
| 123 | H | O(CH₂)₂CH₃ | G | H | R³, R⁴ = O | *4-(N(CH₃)₂)phenoxyhexyl* | H |
| 124 | H | CH₃ | G | H | R³, R⁴ = O | *1-(4-methoxyphenyl)cyclopentyl* | H |
| 125 | H | CH₃ | G | H | R³, R⁴ = O, R⁵, R⁷ = bond | —(CH₂)₁₈CH₃ | H |
| 126 | H | OCH₃ | G | H | R³, R⁴ = O, R⁵, R⁷ = bond | —(CH₂)₁₀CH₃ | H |
| 127 | OCH₃ | H | H | G | R³, R⁴ = O, R⁵, R⁷ = bond | —(CH₂)₁₀CH₃ | H |
| 128 | H | CH₃ | G | CH₃ | R³, R⁴ = O, R⁵, R⁷ = bond | —(CH₂)₇CH₃ | CH₃ |
| 129 | H | Cl | G | H | R³, R⁴ = O, R⁵, R⁷ = bond | *benzyl* | H —(CH₂)₃CH₃ |
| 130 | H | O(CH₂)₂CH₃ | G | H | R³, R⁴ = O, R⁵, R⁷ = bond | *phenethyl* | H |
| 131 | H | OCH₃ | G | H | R³, R⁴ = O, R⁵, R⁷ = bond | *1-phenylcyclopentyl* | H |
| 132 | H | OCH₃ | G | H | R³, R⁴ = O, R⁵, R⁷ = bond | *isobutoxyhexyl chain* | H |

-continued
| Compd. No. | R¹ | R² | X | Y | R³–R⁸ | R⁹ |
|---|---|---|---|---|---|---|
| 133 | H | OCH₃ | G | H | R³, R⁴ = O, R⁵, R⁷ = bond |  |
| 134 | H | OCH₃ | G | H | R³, R⁴ = O, R⁵, R⁷ = bond | 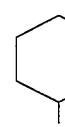 |
| 135 | H | CH₃ | G | CH₃ | R³, R⁴ = O, R⁵, R⁷ = bond | 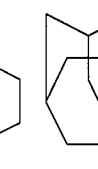 |
| Compd. No. | R¹ | R² | X | Y | R³–R⁸ | R⁹ |
|---|---|---|---|---|---|---|
| 201 | −C(=O)CH₂CH₃ | H | G | H | R³ = CH₃, R⁴ = CH₃ | 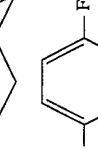 |
| 202 | H | CH₃ | G | H | R³, R⁴ = O | 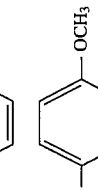 |
| 203 | H | CH₃ | G | H | R³, R⁴ = O | (adamantyl) |
| 204 | H | CH₃ | G | H | R³, R⁴ = O | (4-fluorophenyl) |
| 205 | H | CH₃ | G | H | R³, R⁴ = O | (4-methoxyphenyl) |

-continued

| Compd. No. | R¹ | R² | H | G | X | Y | R³–R⁸ | R¹¹ | R¹² | R¹³ |
|---|---|---|---|---|---|---|---|---|---|---|
| 206 | H | | | | | | R³, R⁴ = O, R⁷ = (CH₂)₂CH₃ | | | ![structure: N-propanoyl-p-tolylamide group] |
| 207 | CH₃ | CH₃ | | | G | H | R⁷ = CH₃, R⁸ = CH₃ | H | H | —(CH₂)₁₇CH₃ |
| 208 | H | OCH₃ | | | G | H | R³ = CH₃, R⁴ = CH₃ | CH₃ | CH₃ | —(CH₂)₉CH₃ |
| 209 | H | H | | | G | OCH₃ | R³ = CH₃, R⁴ = CH₃ | | | —(CH₂)₉CH₃ |
| 210 | H | OCH₃ | | | G | H | R³ = CH₃, R⁴ = CH₃ | H | —(CH₂)₂,₄— | —CH₂CH₂CH=CHCH₂CH=CH(CH₂)₄CH₃ |
| 211 | CH₃ | CH₃ | | | H | G | R³ = CH₃, R⁴ = CH₃ | CH₃ | CH₃ | —(CH₂)₄-phenyl |
| 212 | CH₃ | CH₃ | | | G | H | R³ = CH₃, R⁴ = CH₃ | CH₃ | CH₃ | —(CH₂)₅—O—CH₂—CH(CH₃)₂ (isobutoxy via chain) |
| 213 | H | OCH₃ | | | G | H | R³ = CH₃, R⁴ = CH₃ | CH₃ | CH₃ | —(CH₂)₅—O—C₆H₄—Cl (4-chlorophenoxy) |
| 214 | H | CH₃ | | | G | H | R³ = CH₃, R⁴ = CH₃ | CH₃ | CH₃ | —(CH₂)₅—O—C₆H₄—Cl (4-chlorophenoxy) |
| 215 | H | OCH₃ | | | G | H | R³ = CH₃, R⁴ = CH₃ | CH₃ | CH₃ | —(CH₂)₅—O—C₆H₄—N(CH₃)₂ |
| 216 | H | OCH₃ | | | G | H | R³ = CH₃, R⁴ = CH₃ | CH₃ | CH₃ | —(CH₂)₅—NH—CH(CH₃)₂ |
| 217 | H | CH₃ | | | G | H | R³, R⁴ = O | H | H | —(CH₂)₁₃CH₃ |
| 218 | H | CH₃ | | | G | H | R³, R⁴ = O | CH₃ | CH₃ | —(CH₂)₉CH₃ |
| 219 | H | OCH₃ | | | G | H | R³, R⁴ = O | CH₃ | CH₃ | —(CH₂)₉CH₃ |
| 220 | H | Cl | | | G | H | R³, R⁴ = O | CH₃ | CH₃ | —(CH₂)₉CH₃ |
| 221 | H | CH₂CH₃ | | | G | H | R³, R⁴ = O | CH₃ | CH₃ | —(CH₂)₉CH₃ |
| 222 | H | O(CH₂)₂CH₃ | | | G | H | R³, R⁴ = O | CH₃ | CH₃ | —(CH₂)₉CH₃ |
| 223 | H | OCH₃ | | | G | H | R³, R⁴ = O, R⁷ = CH₂CH₃ | CH₃ | CH₃ | —(CH₂)₉CH₃ |
| 224 | H | CH₃ | | | G | H | R³, R⁴ = O | CH₃ | —(CH₂)₂,₄— | —(CH₂)₉CH₃ |
| 225 | —N(CH₃)₂ | CH₃ | | | G | H | R³, R⁴ = O | CH₃ | —(CH₂)₂,₄— | —(CH₂)₉CH₃ |

-continued

| | | | | | |
|---|---|---|---|---|---|
| 226 | H | CH$_3$ | G H | R$^3$, R$^4$ = O | —(CH$_2$)$_4$— |
| 227 | H | CH$_3$ | G H | R$^3$, R$^4$ = O | CH$_3$, benzyl |
| 228 | H | CH$_3$ | G H | R$^3$, R$^4$ = O | CH$_3$, phenylbutyl |
| 229 | H | OCH$_3$ | G H | R$^3$, R$^4$ = O | CH$_3$, phenylhexyl |
| 230 | H | CH$_3$ | G H | R$^3$, R$^4$ = O | cyclopentane, phenylethyl |
| 231 | H | CH$_3$ | G H | R$^3$, R$^4$ = O | H, —(CH$_2$)$_6$CH=CH(CH$_2$)$_7$CH$_3$ |
| 232 | H | CH$_3$ | G H | R$^3$, R$^4$ = O | CH$_3$, isopentyloxyalkyl |
| 233 | H | CH$_3$ | G H | R$^3$, R$^4$ = O | CH$_3$, isobutoxyalkyl |
| 234 | H | CH$_3$ | G H | R$^3$, R$^4$ = O | CH$_3$, isobutoxyalkyl |
| 235 | H | CH$_3$ | G H | R$^3$, R$^4$ = O | CH$_3$, neopentyloxyalkyl |
| 236 | H | CH$_3$ | G CH$_3$ | R$^3$, R$^4$ = O | CH$_3$, isobutoxyalkyl |
| 237 | H | CH$_3$ | G H | R$^3$, R$^4$ = O | CH$_3$, 4-tert-butylphenoxyalkyl |

-continued

| # | | | | | | | Structure |
|---|---|---|---|---|---|---|---|
| 238 | H | CH₃ | G H | R³, R⁴ = O | CH₃ | CH₃ | 4-pentyloxy-(4-chlorophenyl) |
| 239 | H | CH₃ | G H | R³, R⁴ = O | CH₃ | CH₃ | 4-hexyloxy-(4-chlorophenyl) |
| 240 | H | CH₃ | G CH₃ | R³, R⁴ = O | CH₃ | CH₃ | 4-hexyloxy-(4-chlorophenyl) |
| 241 | H | OCH₃ | G H | R³, R⁴ = O | CH₃ | CH₃ | 4-hexyloxy-(4-chlorophenyl) |
| 242 | H | OCH₃ | G H | R³, R⁴ = O | CH₃ | CH₃ | -(CH₂)₅-O-(4-chlorophenyl) |
| 243 | OCH₃ | OCH₃ | H G | R³, R⁴ = O, R⁷ = CH₃, R⁸ = CH₃ | CH₃ | CH₃ | -(CH₂)₅-O-(4-chlorophenyl) |
| 244 | OCH₃ | H | H G | R³, R⁴ = O, | CH₃ | CH₃ | -(CH₂)₅-O-(4-chlorophenyl) |
| 245 | H | OCH₃ | G H | R³, R⁴ = O, | CH₃ | CH₃ | -(CH₂)₅-O-(4-chlorophenyl) |
| 246 | H | OCH₃ | G H | R³, R⁴ = O, | CH₃ | CH₃ | -(CH₂)₅-O-(4-methylphenyl) |
| 247 | H | CH₃ | G H | R³, R⁴ = O, | CH₃ | CH₃ | -(CH₂)₅-O-(4-N(CH₃)₂-phenyl), piperidinyl-heptyl |

-continued

| # | | | | | |
|---|---|---|---|---|---|
| 248 | H | CH₃ | G H | R³, R⁴ = O, | CH₃ | [N-methylpiperazinyl-alkyl chain] |
| 249 | H | CH₃ | G H | R³, R⁴ = O, | CH₃ | [N-benzylpiperidinyl-alkyl chain] |
| 250 | H | CH₃ | G H | R³, R⁴ = O, | CH₃ | [N-benzylpiperazinyl-alkyl chain] |
| 251 | H | OCH₃ | G H | R³, R⁴ = O, | CH₃ | [4-chlorobenzyl-N(CH₃)-alkyl chain] |
| 252 | H | OCH₃ | G H | R³, R⁴ = O, | CH₃ | [Br-alkyl chain] |
| 253 | NO₂ | H | G H | R³, R⁴ = O, | H | [CO₂CH₂CH₃-alkyl chain] |
| 254 | H | OCH₃ | G H | R³, R⁴ = O, | CH₃ | [4-isobutylphenyl-alkyl chain] |
| 255 | H | OCH₃ | G H | R³, R⁴ = O, R⁵, R⁷ = bond | CH₃ | CH₃ | —(CH₂)₁₃CH₃ |
| 256 | CN | H | G H | R³, R⁴ = O, R⁵, R⁷ = bond | CH₂CH₃ | H | —(CH₂)₇CH₃ |
| 257 | CH₃ | H | H G | R³, R⁴ = O, R⁵, R⁷ = bond | CH₃ | CH₃ | —(CH₂)₉CH₃ |
| 258 | H | H | G H | R³, R⁴ = O, R⁵, R⁷ = bond R⁶ = CH₃, R⁸ = CH₃ | CH₃ | H | —(CH₂)₁₁CH₃ |
| 259 | H | OCH₃ | G H | R³, R⁴ = O, R⁵, R⁷ = bond | —(CH₂)₄— | —(CH₂)₉CH₃ |
| 260 | H | O(CH₂)₂CH₃ | G H | R³, R⁴ = O, R⁵, R⁷ = bond | H | H | [phenyl-alkyl chain] |

-continued

| # | | | | | |
|---|---|---|---|---|---|
| 261 | H | OCH₃ | G  H | R³, R⁴ = O, R⁵, R⁷ = bond | CH₃ | CH₃ | -(CH₂)₅-O-C₆H₄-C(CH₃)₃ (para) |
| 262 | H | OCH₃ | G  H | R³, R⁴ = O, R⁵, R⁷ = bond | CH₃ | CH₃ | -(CH₂)₆-O-C₆H₄-Cl (para) |
| 263 | H | CH₃ | G  H | R³, R⁴ = O, R⁵, R⁷ = bond | CH₃ | CH₃ | -(CH₂)₆-O-C₆H₄-Cl (para) |
| 264 | H | OCH₃ | G  H | R³, R⁴ = O, R⁵, R⁷ = bond; R⁸ = CH₂CH₃ | CH₃ | CH₃ | -(CH₂)₆-O-C₆H₄-N(CH₃)₂ (para) |
| 265 | H | OCH₃ | G  H | R³, R⁴ = O, R⁵, R⁷ = bond | CH₃ | CH₃ | -(CH₂)₉CH₃ |
| 266 | H | OCH₃ | G  H | R³, R⁴ = O, R⁵, R⁷ = bond | CH₃ | CH₃ | -(CH₂)₆-NH-CH₂-C₆H₅ |
| 267 | H | OH | G  H | R³, R⁴ = O, R⁵, R⁷ = bond | CH₃ | CH₃ | -(CH₂)₄-C₆H₄-C(O)CH₃ (meta) |
| 268 | H | F | G  H | R³, R⁴ = O, R⁵, R⁷ = bond | H | H | -CH₂-C₆H₄-NO₂ (para) |

The novel benzopyran derivatives and the pharmaceutically acceptable salts thereof provided by the present invention have an ACAT enzyme inhibitory activity and an excellent pharmacological activity for lowering the total cholesterol and LDL levels of the blood, liver and arterial wall, which renders the useful for treatment of hyperlipidemia and atheroscelerosis.

The benzopyran derivatives and the pharmaceutically acceptable salts thereof according to the present invention can be blended with a pharmacologically acceptable carrier to prepare pharmaceutical compositions. Although the content of the active ingredient in the pharmaceutical composition is not particularly limited, it is usually in the range of from 5 to 70% by weight.

The benzopyran derivatives and the pharmaceutically acceptable salts provided by the present invention can be orally administered.

Examples of dosage forms of the oral preparation include a tablet, a powder, granules and a capsule.

These dosage forms can be shaped according to a conventional method through the use of, for example, an excipient such as lactose, starch or crystalline cellulose, a binder such as carboxymethylcellulose, methyl cellulose or polyvinyl pyrrolidone and a disintegrator such as sodium alginate, sodium hydrogencarbonate or sodium laurate. The powder and granules as well can be shaped in a similar manner. The capsule can be shaped by filling a capsule, such as gelatin, with a powder or granules. Examples of parenteral preparations include percutaneous preparations such as a suppository, a patch and an injection.

Although the dose of the benzopyran derivatives and the pharmaceutically acceptable salts provided by the present invention varies depending upon the severity of disease, age and sex of patient, it is usually about 1 to 500 mg/day/adult.

In the names of compounds described in the present specification, chroman represents 3,4-dihydro-2H-benzopyran, 4-chromanone represents 3,4-dihydro-4-oxo-2H-1-benzopyran, 4-chromanonyl represents 3,4-dihydro-4-oxo-2H-1-benzopyranyl, and chromone represents 4-oxo-4H-1-benzopyran.

EXAMPLES

The present invention will now be further described in more detail by, but is by no means limited to, the following Examples.

Reference Example 1

Synthesis of 7-methoxy-4,4-dimethylchroman-8-yl isocyanate 400 mg of 7-methoxy-4,4-dimethylchroman-8-carboxylic acid was dissolved in dried benzene, and 1.2 ml of oxalyl chloride was added in small portions while stirring at room temperature. After vigorous foaming had quieted down, the system was heated to 60° C., and the reaction was allowed to proceed for 1.5 hr. Excess oxalyl chloride and benzene were removed by distillation under reduced pressure to give an acid chloride (a creamy brown viscous liquid).

165 mg of sodium azide was dried under reduced pressure and dissolved in 6 ml of dimethyl sulfoxide. A solution of the above-described acid chloride in 1.5 ml of dimethyl sulfoxide was dropwise added thereto. After stirring for 30 min, water was added to the reaction mixture, and the mixture was extracted with ethyl acetate. The organic layer was washed with saturated aqueous sodium hydrogencarbonate and dried over anhydrous magnesium sulfate. The dried organic layer was filtered, and the solvent was removed by distillation to give 346 mg of a brown viscous liquid. This liquid was dissolved in 5 ml of o-dichlorobenzene, and the reaction was allowed to proceed at 155° C. for 30 min. o-Dichlorobenzene was removed by distillation under reduced pressure to give 309 mg of the intended title compound.

Property Values:

IR (neat): 3000, 2060, 2270 (NCO), 1605, 1590, 1490, 1435, 1290, 1250, 1190, 1095, 790 cm$^{-1}$.

Reference Example 2

Synthesis of 7-methyl-4-chromanone-8-ylisocyanate 0.15 ml of triethylamine was added to a mixture of 180 mg of 8-amino-7-methyl-4-chromanone, 103 mg of triphosgene and 8 ml of carbon tetrachloride at room temperature with stirring, and the reaction was allowed to proceed under reflux for 6.5 hr. The reaction mixture was cooled to room temperature, ether was added thereto, and insolubles were removed by filtration. The filtrate was concentrated to give 195 mg of the intended title compound.

Reference Example 3

Synthesis of 7-methoxy-4-oxo-4H-1-benzopyran-8-yl isocyanate 122 mg of the intended title compound was produced by using 194 mg of 8-amino-7-methoxychromone in the same manner as that of Reference Example 2.

Example 1

1-Dodecyl-3-(7-methyl-4-chromanon-8-yl)urea
(113)

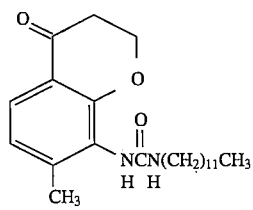

95 mg of dodecylamine was added to a solution of 100 mg of 7-methyl-4-chromanon-8-ylisocyanate in 5 ml of ethyl acetate, and the mixture was stirred at room temperature for 12 hr. The solvent was removed by distillation under reduced pressure, and the residue was recrystallized from ethyl acetate to afford 150 mg of the intended title compound.

Property Values:

$^1$H NMR (CDCl$_3$) δ (ppm): 0.88(t, J=6.6 Hz, 3H), 1.15–1.36 (m, 20H), 2.34 (s, 3H), 2.79 (t, J=6.4 Hz, 2H), 3.22(t, J=6.2 Hz, 2H), 4.55 (t, J=6.4 Hz, 2H), 5.67 (br.s, 1H), 6.92 (d, J=7.9 Hz, 1H), 7.74 (d, J=7.9 Hz, 1H).

m.p.: 161°–165° C.

Examples 2

N-(7-Methoxy-4-chromanon-8-yl)-2,2-dimethyldodecanamide (219)

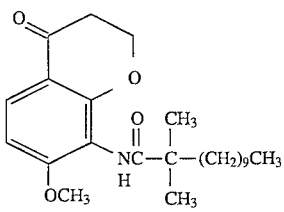

127 mg of 2,2-dimethyldodecanoyl chloride was added to a solution of 98 mg of 8-amino-7-methoxy-4-chromanone and 0.07 ml of triethylamine in 2 ml of dichloromethane, and the mixture was stirred at room temperature for 12 hr. 15 ml of 2N hydrochloric acid was added thereto, and the mixture was extracted with ethyl acetate (25 ml×2). The extract was washed with 25 ml of brine, dried over anhydrous magnesium sulfate, filtered, concentrated and purified by silica gel column chromatography (hexane/ethyl acetate=3:2) to give 198 mg of the intended title compound.

Property Values:

$^1$H NMR (CDCl$_3$) δ (ppm): 0.88 (t, J=5.3 Hz), 1.03–1.70 (m, 18H), 1.30 (s, 6H), 2.77 (t, J=6.6 Hz, 2H), 3.88 (s, 3H), 4.53 (t, J=6.6 Hz, 2H), 6.64(d, J=8.8 Hz, 1H), 6.74(br.s, 1H), 7.84 (d, J=8.8 Hz, 1H).

m.p.: 130°–131° C.

Examples 3 to 54

Synthesis of benzopyran derivatives

Compounds of the present invention were synthesized from corresponding starting compounds and reactants in the same manner as that of Example 1 or Example 2. The property values of the resultant compounds are given in Table 1. Compound Nos. in Table 1 respectively correspond to the Nos. given to compounds listed above as specific preferred examples for this present invention.

TABLE 1

| | Compd. No. | $^1$H NMR data (CDCl$_3$) δ(ppm) | Yield (%) | m.p. (°C.) | Synthetic process |
|---|---|---|---|---|---|
| Ex. 3 | 104 | 0.88(t, J=5.3Hz, 3H), 1.25(br, 20H), 1.34(s, 6H), 1.79(t, J=6.8Hz, 2H), 2.74(t, J=6.8Hz, 2H), 3.20(dt, Jd=5.9Hz, 2H), 3.81(s, 3H), 4.99–5.17(br.s, 1H), 5.79(br.s, 1H), 6.46(d, J=8.6Hz, 1H), 6.88(d, J=8.6Hz, 1H). | 17 | — | according to Example 1 |
| Ex. 4 | 108 | 1.18(s, 6H), 1.54–2.05(m, 10H), 2.68(t, J=6.6Hz, 2H), 3.32(d, J=5.9Hz, 2H), 3.64(s, 3H), 4.71(br.t, J=5.9Hz, 1H), 5.65(br.s, 1H), 6.39(d, J=8.5Hz, 1H), 6.87(d, J=8.5Hz, 1H), 7.04–7.31(m, 5H). | 25 | — | according to Example 1 |
| Ex. 5 | 125 | 0.88(t, J=6.4Hz, 3H), 1.10–1.46(m, 36H), 2.28(s, 3H), 2.75(t, J=6.4Hz, 2H), 3.23(t, J=6.2Hz, 2H), 4.10(br.s, 1H), 4.53(t, J=6.4Hz, 2H), 5.61(br.s, 1H), 6.90(d, J=8.1Hz, 1H), 7.72(d, J=8.1Hz, 1H). | 73 | — | according to Example 1 |
| Ex. 6 | 118 | 1.69–1.88(m, 10H), 2.19(s, 3H), 2.71(t, J=6.8Hz, 2H), 3.32(d, J=5.7Hz, 2H), 4.03(br.s, 1H), 4.43(t, J=6.8Hz, 2H), 5.51(br.s, 1H), 6.85(d, J=8.1Hz, 1H), 7.03–7.18(m, 5H), 7.71(d, J=8.1Hz, 1H). | 61 | 210–217 | according to Example 1 |
| Ex. 7 | 124 | 1.64–1.97(m, 8H), 2.21(s, 3H), 2.72(t, J=6.4Hz, 2H), 3.30(d, J=5.5Hz, 2H), 3.75(s, 3H), 3.98–4.12(br, 1H), 4.43(t, J=6.4Hz, 2H), 5.56(s, 1H), 6.69(d, J=8.9Hz, 2H), 6.86(d, J=8.2Hz, 1H), 7.01(d, J=8.9Hz, 2H), 7.72(d, J=8.2Hz, 1H). | 62 | 171.5–173 | according to Example 1 |
| Ex. 8 | 119 | 1.45–2.30(m, 8H), 2.43(s, 3H), 2.75(t, J=6.4Hz, 2H), 3.58(s, 2H), 3.87(s, 3H), 4.52(t, J=6.4Hz, 2H), 5.37(br.s, 1H), 6.63(d, J=9.0Hz, 1H), 7.05–7.40(m, 5H), 7.84(d, J=9.0Hz, 1H). | 56 | — | according to Example 1 |
| Ex. 9 | 117 | 0.87(t, J=5.5Hz, 3H), 1.2–1.4(m, 4H), 2.75(t, J=6.6Hz, 2H), 3.25(t, J=6.4Hz, 2H), 3.88(s, 3H), 4.52(t, J=6.6Hz, 2H), 4.54(s, 2H), 5.42(br.s, 1H), 6.63(d, J=9.0Hz, 1H), 7.24(s, 5H), 7.84(d, J=9.0Hz). | 67 | — | according to Example 1 |
| Ex. 10 | 126 | 0.75–1.00(m, 3H), 1.1–1.7(m, 20H), 3.25(t, J=6.6Hz, 2H), 3.98(s, 3H), 4.3(br.s, 1H), 5.83(br.s, 1H), 6.28(d, J=6.2Hz, 1H), 7.06(d, J=9.0Hz, 1H), 7.82(d, J=6.2Hz, 1H), 7.81(d, J@9.0Hz, 1H). | 70 | 197–200 | according to Example 1 |
| Ex. 11 | 131 | 1.4–2.2(m, 8H), 3.37(d, J=5.7Hz, 2H), 3.85(s, 3H), 4.3(br.t, 1H), 5.7(br.s, 1H), 6.27(d, J=6.2Hz, 1H), 6.98(d, J=9.0Hz, 1H), 7.13(s, 5H), 7.74(d, J=6.2Hz, 1H), 8.09(d, J=9.0Hz, 1H). | 40 | 180–182 | according to Example 1 |
| Ex. 12 | 134 | 1.67–2.04(m, 8H), 3.33(d, J=5.7Hz, 2H), 3.75(s, 3H), 3.87(s, 3H), 4.18–4.30(br, 1H), 5.65(br.s, 1H), 6.27(d, J=5.9Hz, 1H), 6.71(d, J=8.9Hz, 2H), 6.99(d, J=8.9Hz, 2H), 6.99(d, J=9.0Hz, 1H), 7.74(d, J=5.9Hz, 1H), 8.09(d, J=9.0Hz, 1H). | 52 | 162–164 | according to Example 1 |
| Ex. 13 | 209 | 0.87(t, J=5.3Hz, 3H), 1.08–1.47(m, 16H), 1.39(s, 6H), 1.53–1.80(m, 8H), 1.82(t, J=6.6Hz, 2H), 2.05–2.30(m, 2H), 2.60(t, J=6.6Hz, 2H), 3.82(s, 3H), 6.71(d, J=8.6Hz, 1H), 6.93(br.s, 1H), 7.08(d, J=8.6Hz, 1H). | 50 | — | according to Example 2 |
| Ex. 14 | 204 | 2.32(s, 3H), 2.76(t, J=6Hz, 2H), 4.52(t, J=6Hz, 2H), 6.8–7.3(m, 3H), 7.55(br.s, 1H), 7.6–8.1(m, 3H). | 88 | 178–179 | according to Example 2 |
| Ex. 15 | 205 | 2.33(s, 3H), 2.76(t, J=6Hz, 2H), 3.88(s, 3H), 4.52(t, J=6Hz, 2H), 6.8–7.1(m, 3H), 7.5(br.s, 1H), 7.6–8.0(m, 3H). | 59 | 189–189.5 | according to Example 2 |
| Ex. 16 | 202 | 1.2–2.6(m, 11H), 2.25(s, 3H), 2.76(t, J=6Hz, 2H), 2.54(t, J=6Hz, 2H), 6.80–7.05(m, 2H), 7.73(d, J=8Hz, 1H). | 29 | 187–188 | according to Example 2 |
| Ex. 17 | 203 | 1.7–2.4(m, 18H), 2.76(t, J=6Hz, 2H), 4.52(t, J=6Hz, 2H), 6.87(d, J=8Hz, 1H), 7.10(br.s, 1H), 7.68(d, J=8Hz, 1H). | 47 | 210–212 | according to Example 2 |
| Ex. 18 | 217 | 0.88(t, J=5.3Hz, 3H), 1.13–1.83(m, 26H), 2.12–2.38(m, 2H), 2.26(s, 3H), 2.77(t, J=6.6Hz, 2H), 4.53(t, J=6.6Hz, 2H), 6.89(d, J=8.1Hz, 1H), 6.94(br.s, 1H), 7.70(d, J=8.1Hz, 1H). | 40 | — | according to Example 2 |
| Ex. 19 | 218 | 0.8–1.8(m, 27H), 2.24(s, 3H), 2.76(t, J=6Hz, 2H), 4.53(t, J=6Hz, 2H), 6.88(d, J=8Hz, 1H), 7.00(br.s, 1H), 7.69(d, J=8Hz, 1H). | 89 | 80–81 | according to Example 2 |

TABLE 1-continued

| | Compd. No. | $^1$H NMR data (CDCl$_3$) δ(ppm) | Yield (%) | m.p. (°C.) | Synthetic process |
|---|---|---|---|---|---|
| Ex. 20 | 224 | 0.88(t, J=6.4Hz, 3H), 1.14–1.38(m, 16H), 1.46–1.56(m, 8H), 2.18–2.52(m, 2H), 2.28(s, 3H), 2.77(t, J=6.8Hz, 2H), 4.55(t, J=6.8Hz, 2H), 6.76(br.s, 1H), 6.91(d, J=8.1Hz, 1H), 7.73(d, J=8.1Hz, 1H). | 88 | 61–62 | according to Example 2 |
| Ex. 21 | 231 | 0.88(t, J=5.5Hz, 3H), 1.1–1.8(m, 22H), 1.85–2.2(m, 4H), 2.25(s, 3H), 2.35(t, J=6.8Hz, 2H), 2.77(t, J=6.6Hz, 2H), 4.54(t, J=6.6Hz, 2H), 5.34(t, J=5Hz, 2H), 6.89(d, J=8Hz, 1H), 6.98(br.s, 1H), 7.71(d J=8Hz, 1H). | 85 | — | according to Example 2 |
| Ex. 22 | 226 | 1.57–2.29(m, 6H), 2.11(s, 3H), 2.51–2.76(m, 2H), 2.70(t, J=6.4Hz, 2H), 4.38(t, J=6.4H, 2H), 6.54(br.s, 1H), 6.82(d, J=8.0Hz, 1H), 7.28–7.57(m, 5H), 7.65(d, J=8.0Hz, 1H). | 77 | 185–187 | according to Example 2 |
| Ex. 23 | 227 | 1.34(s, 6H), 2.18(s, 3H), 2.73(t, J=6Hz, 2H), 2.97(s, 2H), 4.44(t, J=6Hz, 2H), 6.80–7.05(m, 2H), 7.23(s, 5H), 7.69(d, J=8Hz, 1H). | 87 | 136 | according to Example 2 |
| Ex. 24 | 230 | 1.5–2.3(m, 11H), 2.73(t, J=6.6Hz, 2H), 3.06(s, 2H), 4.23(t, J=6.6Hz, 2H), 6.75–7.00(m, 2H), 7.24(s, 5H), 7.68(d, J=8Hz, 1H). | 89 | 141–142 | according to Example 2 |
| Ex. 25 | 228 | 1.0–1.8(m, 8H), 1.31(s, 6H), 2.24(s, 3H), 2.45–2.85(m, 4H), 4.46(t, J=6.0Hz, 2H), 6.89(d, J=8.5Hz, 1H), 7.0(br.s, 1H), 7.1–7.4(m, 5H), 7.70(d, J=8.5Hz, 1H). | 100 | 90–97 | according to Example 2 |
| Ex. 26 | 233 | 0.87(d, J=6.2Hz, 6H), 1.00–1.85(m, 11H), 1.32(s, 6H), 2.25(s, 3H), 2.77(t, J=6.6Hz, 2H), 2.37(t, J=6.4Hz, 4H), 4.54(t, J=6.6Hz, 2H), 6.89(d, J=8.1H, 1H), 7.03(br.s, 1H), 7.71(d, J=8.1H, 1H). | 80 | oleaginous substance | according to Example 2 |
| Ex. 27 | 234 | 0.89(d, J=6.6Hz, 6H), 1.20–2.05(m, 11H), 1.32(s, 6H), 2.25(s, 3H), 2.77(t, J=6.4Hz, 2H), 3.15(s, 2H), 3.39(t, J=6.1Hz, 2H), 4.54(t, J=6.4Hz, 2H), 6.90(d, J=8.1Hz, 1H), 6.99(br.s, 1H), 7.71(d, J=8.1Hz, 1H). | 70 | oleaginous substance | according to Example 2 |
| Ex. 28 | 235 | 0.89(s, 9H), 1.20–1.78(m, 10H), 1.32(s, 6H), 2.25(s, 3H), 2.77(t, J=6.6Hz, 2H), 3.03(s, 2H), 3.39(t, J=5.9Hz, 2H), 4.54(t, J=6.6 Hz, 2H), 6.90(d, J=8.1Hz, 1H), 6.99(br.s, 1H), 7.71(d, J=8.1Hz, 1H). | 18 | oleaginous substance | according to Example 2 |
| Ex. 29 | 232 | 0.88(d, J=6.2Hz, 6H), 0.99–1.82(m, 15H), 1.31(s, 6H), 2.25(s, 3H), 2.77(t, J=6.6Hz, 2H), 3.37(t, J=6.6Hz, 2H), 3.39(t, J=6.4Hz, 2H), 4.53(t, J=6.6Hz, 2H), 6.89(d, J=8.2Hz, 1H), 6.99(br.s, 1H), 7.70(d, J=8.2Hz, 1H). | 67 | oleaginous substance | according to Example 2 |
| Ex. 30 | 237 | 1.29(s, 9H), 1.34(s, 6H), 1.4–1.9(m, 6H), 2.25(s, 3H), 2.72(t, J=6Hz, 2H), 3.96(t, J=6Hz, 2H), 4.49(t, J=6Hz, 2H), 6.7–7.1(m, 4H), 7.27(d, J=9.0Hz, 2H), 7.70(d, J=8.1Hz, 1H). | 100 | 115–116 | according to Example 2 |
| Ex. 31 | 238 | 1.1–2.0(m, 6H), 1.34(s, 6H), 2.25(s, 3H), 2.74(t, J=6.4Hz, 2H), 3.94(t, 2H, J=6Hz), 4.50(t, J=6.4Hz, 2H), 6.7–7.2(m, 4H), 7.20(d, J=8.8Hz, 2H), 7.70(d, J=8.1Hz, 1H). | 87 | oleaginous substance | according to Example 2 |
| Ex. 32 | 239 | 1.10–1.95(m, 8H), 1.33(s, 6H), 2.24(s, 3H), 2.74(t, J=6.1Hz, 2H), 3.92(t, J=6.2Hz, 2H), 4.51(t, J=6.1Hz, 2H), 6.8–7.3(m, 6H), 7.70(d, J=8.2Hz, 1H). | 78 | 94 | according to Example 2 |
| Ex. 33 | 247 hydrochloride | 1.32(s, 6H), 1.36–2.01(m, 16H), 2.02–2.83(m, 3H), 2.25(s, 3H), 2.78(t, J=6.4Hz, 2H), 2.78–2.97(m, 2H), 3.05–3.75(m, 2H), 4.55(t, J=6.4Hz, 2H), 6.89(d, J=8.1Hz, 1H), 7.16(s, 1H), 7.71(d, J=8.1Hz, 1H). | 9 | 131–134 | according to Example 2 |
| Ex. 34 | 248 hydrochloride | 1.26–1.96(m, 16H), 2.25(s, 3H), 2.73–3.20(m, 7H), 3.23(m, 10H), 4.56(t, J=6.4Hz, 2H), 6.91(d, J=8.4Hz, 1H), 7.08(s, 1H), 7.71(d, J=8.4Hz, 1H). | 22 | 171.5–173 | according to Example 2 |
| Ex. 35 | 249 | 1.31(s, 6H), 1.36–1.80(m, 6H), 2.24(s, 3H), 2.28–2.45(m, 10H), 2.75(t, J=6.4Hz, 2H), 3.45(s, 2H), 4.52(t, J=6.4Hz, 2H), 6.89(d, J=8.1Hz, 1H), 7.13(s, 1H), 7.28(s, 5H), 7.71(d, J=8.1Hz, 1H). | 46 | oleaginous substance | according to Example 2 |
| Ex. 36 | 250 | 1.22–1.47(m, 16H), 2.24(s, 3H), 2.30–2.33(m, 2H), 2.47(s, 8H), 2.76(s, J=6.4Hz, 2H), 3.50(s, 2H), 4.53(t, J=6.4Hz, 2H), 6.89(d, J=8.2Hz, 1H), 7.00(s, 1H), 7.29(s, 5H), 7.70(d, J=8.2Hz, 1H). | 31 | — | according to Example 2 |
| Ex. 37 | 252 | 1.30(s, 6H), 1.30–2.05(m, 10H), 2.76(t, J=6.4Hz, 2H), 3.40(t, J=6.6Hz, 2H), 3.87(s, 3H), 4.52(t, J=6.4Hz, 2H), 6.63(d, J=9.0Hz, 1H), 6.78(s, 1H), 7.83(d, J=9.0Hz, 1H). | 41 | 127–129 | according to Example 2 |
| Ex. 38 | 229 | 1.0–1.8(m, 16H), 2.45–2.85(m, 4H), 3.83(s, 3H), 4.45(t, J=6.8Hz, 2H), 6.62(d, J=9.0H, 1H), 6.7(br.s, 1H), 7.1–7.3(m, 5H), 7.84(d, J=9.0Hz, 1H). | 86 | 101–102 | according to Example 2 |
| Ex. 39 | 254 | 0.89(d, J=6.6Hz, 6H), 1.38(s, 6H), 1.45–1.95(m, 5H), 2.25–2.75(m, 4H), 2.75(t, J=6.4H, 2H), 3.86(s, 3H), 4.50(t, J=6.4Hz, 2H), 6.78(d, J=9.0Hz, 1H), 6.80(br.s, 1H), 7.05(m, 4H), 7.84(d, J=9.0Hz, 1H). | 87 | — | according to Example 2 |
| Ex. 40 | 245 | 1.0–1.9(m, 10H), 1.30(s, 6H), 2.27(s, 3H), 2.75(t, J=6.6Hz, 2H), 3.87(s, 3H), 3.92(t, J=6.2Hz, 2H), 4.58(t, J=6.6Hz, 2H), 6.63(d, J=8.6Hz, 1H), 6.76(d, J=9.0Hz, 2H), 7.05(d, J=9.0Hz, 2H), 7.84(d, J=8.6Hz, 1H). | 63 | 105–106 | according to Example 2 |
| Ex. 41 | 241 | 1.25–1.95(m, 8H), 1.31(s, 6H), 2.75(t, J=6.4Hz, 2H), 3.86(s, 3H), 3.92(t, J=6.2Hz, 2H), 4.50(t, J=6.4Hz, 2H), 6.63(d, J=9.0Hz, 1H), 6.79(d, J=9.0Hz, 2H), 6.82(s, 1H), 7.21(d, J=9.0Hz, 2H), 7.84(d, J=9.0Hz, 1H). | 55 | 90–91 | according to Example 2 |
| Ex. 42 | 242 | 1.27–1.95(m, 10H), 1.30(s, 6H), 2.75(t, J=6.4Hz, 2H), 3.87(s, 3H), 3.91(t, J=5.9Hz, 2H), 4.51(t, J=6.4Hz, 2H), 6.63(d, J=9.0Hz, 1H), 6.73(s, 1H), 6.79(d, J=9.0Hz, 2H), 7.21(d, J=9.2Hz, 2H), 7.84(d, J=9.0Hz, 1H). | 34 | 89–90 | according to Example 2 |
| Ex. 43 | 236 | 0.89(d, J=6.6Hz, 6H), 1.12–1.96(m, 10H), 1.30(s, 6H), 2.20(s, 3H), 2.58(s, 3H), 2.75(t, J=6.6Hz, 2H), 3.15(t, J=6.6Hz, 2H), 3.39(t, J=6.4Hz, 2H), 4.48(t, J=6.6Hz, 2H), 6.68(s, 1H), 6.95(br.s, 1H). | 75 | oleaginous substance | according to Example 2 |
| Ex. 44 | 240 | 1.03–1.97(m, 8H), 1.32(s, 6H), 2.19(s, 3H), 2.58(s, 3H), 2.73(t, J=6.6Hz, 2H), 3.92(t, J=5.9Hz, 2H), 4.46(t, J=6.6Hz, 2H), 6.68(s, 1H), 6.79(d, J=9.0Hz, 2H), 6.95(br.s, 1H), 7.20(d, J=9.0Hz, 2H). | 96 | 95–96 | according to Example 2 |
| Ex. 45 | 244 | 1.3–1.9(m, 10H), 1.37(s, 6H), 2.76(t, J=6.5Hz, 2H), 3.81(s, 3H), 3.90(t, J=6Hz, 2H), 4.43(t, J=6Hz, 2H), 6.7–6.9(m, 3H), 7.1–7.3(m, 3H), | 86 | 76–77 | according to Example 2 |

TABLE 1-continued

| Compd. No. | ¹H NMR data (CDCl₃) δ(ppm) | Yield (%) | m.p. (°C.) | Synthetic process |
|---|---|---|---|---|
| Ex. 46 | 243 | 9.6(br.s, 1H). 1.3–1.9(m, 10H), 1.33(s, 6H), 1.42(s, 6H), 2.61(s, 2H), 3.79(s, 3H), 3.86(s, 3H), 3.89(t, J=6.3Hz, 2H), 6.25(s, 1H), 6.79(d, J=9Hz, 2H), 7.21(d, J=9Hz, 2H), 9.7(br.s, 1H). | 96 | 42–45 | according to Example 2 |
| Ex. 47 | 220 | 0.88(t, J=6.1Hz, 3H), 1.00–1.76(m, 18H), 1.32(s, 3H), 2.81(t, J=6.4Hz, 2H), 4.56(t, J=6.4Hz, 2H), 6.94(br.s, 1H), 7.09(d, J=8.6Hz, 1H), 7.76(d, J=6.4Hz, 1H). | 91 | oleaginous substance | according to Example 2 |
| Ex. 48 | 222 | 0.88(t, J=5.7Hz, 3H), 1.02(t, J=7.0Hz, 3H), 1.14–1.57(m, 18H), 1.30(s, 6H), 1.77(tq, J=7.0, 6.4Hz, 2H), 2.77(t, J=6.4Hz, 2H), 4.00(t, J=6.4Hz, 2H), 4.52(t, J=6.4Hz, 2H), 6.61(d, J=8.8Hz, 1H), 6.76(s, 1H), 7.82(d, J=8.8Hz, 1H). | 70 | 131–133 | according to Example 2 |
| Ex. 49 | 255 | 0.88(t, J=5.1Hz, 3H), 1.1–1.9(m, 26H), 2.43(t, J=6.8Hz, 2H), 3.96(s, 3H), 6.27(d, J=5.9Hz, 1H), 6.75(br.s, 1H), 7.04(d, J=9.0Hz, 1H), 7.78(d, J=5.9Hz, 1H), 8.14(d, J=9.0Hz, 1H). | 85 | 115–118 | according to Example 2 |
| Ex. 50 | 259 | 0.88(t, J=5.3Hz, 3H), 1.1–1.9(m, 24H), 2.0–2.3(m, 2H), 3.95(s, 3H), 6.26(d, J=6.2Hz, 1H), 6.90(br.s, 1H), 7.04(d, J=9.0Hz, 1H), 7.75(d, J=6.2Hz, 1H), 8.12(d, J=9.0Hz, 1H). | 77 | amorphous | according to Example 2 |
| Ex. 51 | 261 | 1.29(s, 9H), 1.36(s, 6H), 1.50–1.95(m, 6H), 3.75–4.05(m, 5H), 6.22(d, J=6.2Hz, 1H), 6.79(d, J=6.8Hz, 2H), 7.0(br.s, 1H), 7.03(d, J=7.0Hz, 1H), 7.28(d, J=6.8Hz, 2H), 7.72(d, J=6.2Hz, 1H), 8.11(d, J=7.0Hz, 1H). | 78 | amorphous | according to Example 2 |
| Ex. 52 | 262 | 1.2–2.0(m, 8H), 1.35(s, 6H), 3.93(t, J=6.0Hz, 2H), 3.93(s, 3H), 6.24(d, J=6.2Hz, 1H), 6.79(d, J=9.0Hz, 2H), 6.95(br.s, 1H), 7.03(d, J=9.0Hz, 1H), 7.21(d, J=9.0Hz, 2H), 7.72(d, J=6.2Hz, 1H), 8.12(d, J=9.0Hz, 1H). | 63 | 66–68 | according to Example 2 |
| Ex. 53 | 263 | 1.10–1.95(m, 8H), 1.37(s, 6H), 2.34(s, 3H), 3.92(t, J=6.0Hz, 2H), 6.28(d, J=5.9Hz, 1H), 6.79(d, J=9.0Hz, 2H), 7.2(br.s, 1H), 7.21(d, J=9.0Hz, 2H), 7.26(d, J=8.4Hz, 1H), 7.74(d, J=8.9Hz, 1H), 8.01(d, J=8.4Hz, 1H). | 76 | 94–96 | according to Example 2 |
| Ex. 54 | 264 | 0.88(t, J=5.5Hz, 3H), 1.07–1.80(m, 27H), 2.49(q, J=7.5Hz, 2H), 3.79(s, 3H), 5.92(s, 1H), 6.79(d, J=8.9Hz, 1H), 7.54(s, 1H), 7.84(d, J=8.9Hz, 1H). | 67 | oleaginous substance | according to Example 2 |

Example 55

N-(7-Methoxy-4-chromanon-8-yl)-2,2-dimethyl-8-p-dimethylaminophenoxyoctaneamide (246)

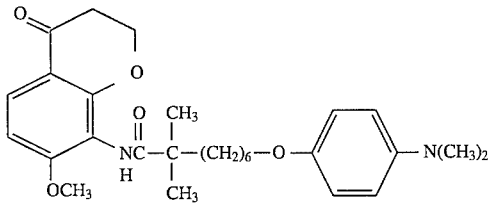

49 mg of p-nitrophenol and 49 mg of potassium carbonate were added to a solution of 150 mg of N-(7-methoxy-4-chromanon-8-yl)-2,2-dimethyl-8-bromooctaneamide (252) in acetonitrile (5 ml), and the mixture was heated under reflux for 15 hr. 10 ml of water was added to the reaction mixture, and the mixture was made alkaline with 2N aqueous NaOH solution and extracted with ethyl acetate. The extract was washed with water and brine, dried over anhydrous magnesium sulfate, and the solvent was removed by distillation to give N-(7-methoxy-4-chromanon-8-yl)-2,2-dimethyl-8-p-nitrophenoxyoctaneamide. This product was dissolved in 10 ml of ethyl acetate, 50 mg of Pd-C (10%) was added thereto, and the mixture was stirred under hydrogen. The Pd catalyst was removed by filtration, and the solvent was removed to give N-(7-methoxy-4-chromanon-8-yl)-2,2-dimethyl-8-p-aminophenoxyoctaneamide. This product was dissolved in 10 ml of ethanol, 50 mg of PtO₂ and 500 mg of 37% aqueous formaldehyde solution were added thereto, and the mixture was stirred under hydrogen at room temperature for 15 hr. The catalyst was removed by filtration, the filtrate was concentrated, and purified by silica gel column chromatography (ethyl acetate/hexane=1:1) to give 34 mg of the intended title compound. Ethanol in which a HCl gas had been dissolved was added thereto, and the solvent was removed by distillation to give a hydrochloride.

Property Values:

¹H NMR (CDCl₃) δ (ppm): 1.2–1.9 (m, 10H), 1.30 (s, 6H), 2.82 (t, J=6 Hz, 2H), 3.86(s, 3H), 3.89 (t, J=6 Hz, 2H), 4.50 (t, J=6 Hz, 2H), 6.62 (d, J=9 Hz, 1H), 6.7–6.9 (m, 5H), 7.83(d, J=9 Hz, 1H).

Example 56

Measurement of ACAT enzyme inhibitory activity (measurement of ACAT enzyme inhibitory activity of rabbit intestinal mucosa)

Preparation of a domestic rabbit intestinal mucosa microsome and measurement of the ACAT enzyme activity were conducted by slightly modifying a method established by Salone and Field (see Biochemica et Biophysica, vol. 712, 557 (1982). The domestic rabbit intestinal mucosa was homogenized by using a 40 mM phosphate buffer having a pH value of 7.4 (buffer A) containing 30 mM EDTA, 50 mM KCl and 0.1M sucrose and centrifuged at 10,000×g and a temperature of 4° C. for 30 min to provide a supernatant. The supernatant was further centrifuged at 105,000×g and a temperature of 4° C. for one hr to provide a precipitate. The precipitate was resuspended in the buffer A to provide a microsome fraction.

1% v/v of a dimethylsulfoxide solution of each specimen compound in a predetermined concentration was added to the buffer A containing 43 μM serum albumin and 0.5 mg/ml microsome fraction, and the mixture was heated at 37° C. for 5 min.

Then, 43 μM oleoyl CoA containing [1-¹⁴C] oleoyl CoA (3.7 kB) was added thereto, the mixture was heated at 37° C. for 10 min, and chloroform/methanol (2/1) containing 10 mg/ml cholesteryl oleate was added thereto to terminate the reaction.

0.111 kB of [3H] cholesteryl oleate and 1N hydrochloric acid were added thereto, and the mixture was stirred. The cholesteryl oleate extracted into the chloroform layer was isolated by a thin-layer chromatography, and the radioactivity was measured as the ACAT activity. The results are given in Table 2.

TABLE 2

| Test Compound | ACAT Inhibitory Activity, $IC_{50}$ (M) |
|---|---|
| Compound of Ex. 1 | $7.3 \times 10^{-8}$ |
| Compound of Ex. 2 | $1.3 \times 10^{-8}$ |
| Compound of Ex. 3 | $3.4 \times 10^{-7}$ |
| Compound of Ex. 4 | $6.9 \times 10^{-7}$ |
| Compound of Ex. 6 | $5.3 \times 10^{-7}$ |
| Compound of Ex. 7 | $5.0 \times 10^{-7}$ |
| Compound of Ex. 10 | $3.3 \times 10^{-7}$ |
| Compound of Ex. 13 | $1.2 \times 10^{-6}$ |
| Compound of Ex. 18 | $7.8 \times 10^{-9}$ |
| Compound of Ex. 19 | $2.1 \times 10^{-7}$ |
| Compound of Ex. 20 | $1.7 \times 10^{-7}$ |
| Compound of Ex. 25 | $2.5 \times 10^{-7}$ |
| Compound of Ex. 26 | $3.4 \times 10^{-7}$ |
| Compound of Ex. 27 | $9.0 \times 10^{-8}$ |
| Compound of Ex. 28 | $5.4 \times 10^{-8}$ |
| Compound of Ex. 29 | $2.0 \times 10^{-7}$ |
| Compound of Ex. 30 | $5.0 \times 10^{-8}$ |
| Compound of Ex. 31 | $5.1 \times 10^{-7}$ |
| Compound of Ex. 32 | $4.7 \times 10^{-7}$ |
| Compound of Ex. 37 | $2.5 \times 10^{-8}$ |
| Compound of Ex. 38 | $4.4 \times 10^{-8}$ |
| Compound of Ex. 40 | $4.3 \times 10^{-8}$ |
| Compound of Ex. 41 | $5.2 \times 10^{-8}$ |
| Compound of Ex. 42 | $6.4 \times 10^{-8}$ |
| Compound of Ex. 43 | $9.0 \times 10^{-8}$ |
| Compound of Ex. 44 | $4.0 \times 10^{-7}$ |
| Compound of Ex. 45 | $1.8 \times 10^{-7}$ |
| Compound of Ex. 47 | $1.5 \times 10^{-7}$ |
| Compound of Ex. 48 | $1.4 \times 10^{-8}$ |
| Compound of Ex. 49 | $5.2 \times 10^{-8}$ |
| Compound of Ex. 50 | $2.7 \times 10^{-7}$ |
| Compound of Ex. 51 | $1.9 \times 10^{-7}$ |
| Compound of Ex. 52 | $1.6 \times 10^{-7}$ |
| Compound of Ex. 54 | $7.8 \times 10^{-7}$ |
| Compound of Ex. 55 | $8.1 \times 10^{-8}$ |
| Compound of Ex. 9 in Japanese Unexamined Patent Publication (Kokai) No. 63-253060 | $1.4 \times 10^{-7}$ |

All the test compounds had a $LD_{50}$ value of 2 g/kg or more (mouse).

Example 57

Percentage change of serum cholesterol

Male Wistar rats having a weight of 200 g were preliminarily bred for 7 days while they freely ingested a normal feed (CE-2 manufactured by CLEA Japan Inc.).

Thereafter, they were bred for 3 days while they freely ingested a feed enriched with cholesterol and fat (2% cholesterol, 1% cholic acid, 20% casein, 45% fine granulated sugar, 12% coconut oil, 4% KC flock, 1% mixed vitamin, 7% mixed mineral and 8% dried fish powder; a product of CLEA Japan Inc.). During the cholesterol loading period, the test compound of the present invention was orally administered to the above test animals at a dose of 10 mg per kg of the weight once a day for three days. On the other hand, the excipient alone was administered to the control animals.

8 hr after the last administration, the test animals were fasted. 16 hr after the initiation of the fasting, these test animals were slaughtered. The serum cholesterol level was measured for each animal.

The results were compared with those of the control and are given as percentage serum cholesterol (%) in Table 3.

Percentage change of serum cholesterol (%)={(A−B)/B}×100 wherein A represents the total cholesterol level of serum in the group of rats to which the test compound was administered; and B represents the total cholesterol level of serum in the control group of rats.

TABLE 3

| Test Compound | Percentage Change of Serum Cholesterol (%) |
|---|---|
| Compound of Ex. 19 | −27 |
| Compound of Ex. 20 | −29 |
| Compound of Ex. 25 | −32 |
| Compound of Ex. 28 | −31 |
| Compound of Ex. 29 | −22 |
| Compound of Ex. 32 | −33 |
| Compound of Ex. 41 | −40[1] |
| Compound of Ex. 42 | −51[1] |
| Compound of Ex. 50 | −27 |
| Compound of Ex. 52 | −17[2] |

Note:
[1] 1 mg/kg
[2] 3 mg/kg

Example 58

Preparation of Tablet

A tablet containing 30 mg of the compound of Example 1 was prepared according to the following formulation.

| Compound Ex. 1 | 30 mg |
|---|---|
| Lactose | 87 mg |
| Starch | 30 mg |
| Magnesium stearate | 3 mg |

Utilization in Industry

The present invention provides novel benzopyran derivatives and their pharmaceutically acceptable salts such as novel chroman derivative, chromanone derivative and chromone derivative. As described above, these benzopyran derivatives are useful as ACAT inhibitor, anti-hyperlipidemia agent and anti-arteriosclerosis agent compositions.

We claim:

1. A benzopyrran derivative represented by the formula (I) or its pharmaceutically acceptable salt:

(I)

wherein either one of X and Y represents the following formula (A):

$$-NH-\overset{O}{\overset{\|}{C}}(\!-\!N\!)_{\overline{n}}R^9$$
$$\phantom{-NH-C(-N)_{\overline{n}}}\!|$$
$$\phantom{-NH-C(-N)_{\overline{n}}}R^{10}$$

(A)

and the other of X and Y, which is not according to formula (A), represents a substituent as defined for $R^1$ and $R^2$;

$R^1$ and $R^2$ each independently represent a hydrogen atom, a halogen atom, an unsubstituted $C_1$–$C_6$ lower alkyl group, or an unsubstituted $C_1$–$C_6$ lower alkoxy group;

$R^3$ and $R^4$ combine to represent an oxygen atom;

$R^5$, $R^6$, $R^7$ and $R^8$ each independently represent a hydrogen atom or an unsubstituted $C_1$–$C_3$ lower alkyl group;

$R^9$ represents a phenyl group substituted with a halogen atom or a methoxy group, an unsubstituted $C_5$–$C_{10}$ cycloalkyl group, or a group represented by the formula:

wherein $R^{11}$ and $R^{12}$ each independently represent a hydrogen atom or an unsubstituted $C_1$–$C_6$ lower alkyl group, provided that $R^{11}$ and $R^{12}$ may be combined with each other to form a $C_3$–$C_7$ carbon ring; and $R^{13}$ represents a $C_5$–$C_{19}$ chain alkyl or alkenyl group optionally substituted with a halogen atom, an unsubstituted phenyl group, a $C_7$–$C_{12}$ arylalkyl group optionally substituted with a methoxy group, a $C_1$–$C_5$ lower alkyl group or a dimethylamino group, or a group represented by the formula:

wherein A represents a $C_1$–$C_8$ alkyl group, Z represents an oxygen atom or a group represented by the formula:

wherein $R^{14}$ represents a hydrogen atom, a $C_1$–$C_6$ lower alkyl group, or a $C_1$–$C_6$ lower acyl group; and B represents an unsubstituted $C_1$–$C_8$ alkyl group, a phenyl group optionally substituted with a $C_1$–$C_6$ lower alkyl group or a halogen atom;

$R^{10}$ represents a hydrogen atom or a $C_1$–$C_6$ lower alkyl group; and n is 0 or 1.

2. A benzopyran derivative and its pharmaceutically acceptable salt according to claim 1, wherein the n value in the formula (I) is 1.

3. A benzopyran derivative and its pharmaceutically acceptable salt according to claim 2, wherein the $R^3$ and $R^4$ in the formula (I) each independently represent a hydrogen atom or an unsubstituted $C_1$–$C_3$ lower alkyl group.

4. A benzopyran derivative and its pharmaceutically acceptable salt according to claim 2, wherein the $R^3$ and $R^4$ in the formula (I) are combined with each other to represent an oxygen atom and the $R^5$ and $R^7$ are not combined with each other to represent a carbon-carbon bond.

5. A benzopyran derivative and its pharmaceutically acceptable salt according to claim 2, wherein the $R^3$ and $R^4$ in the formula (I) are combined with each other to represent an oxygen atom and the $R^5$ and $R^7$ are combined with each other to represent a carbon-carbon bond.

6. A benzopyran derivative and its pharmaceutically acceptable salt according to claim 1, wherein the n value in the formula (I) is 0 (zero).

7. A benzopyran derivative and its pharmaceutically acceptable salt according to claim 6, wherein the $R^3$ and $R^4$ in the formula (I) each independently represent a hydrogen atom or an unsubstituted $C_1$–$C_3$ lower alkyl group.

8. A benzopyran derivative and its pharmaceutically acceptable salt according to claim 7, wherein $R^9$ in the formula (I) is a group represented by the formula:

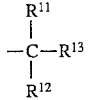

wherein any one of $R^{11}$ and $R^{12}$ represents a $C_1$–$C_6$ lower alkyl group or $R^{11}$ and $R^{12}$ are combined with each other to form a $C_3$–$C_7$ carbon ring.

9. A benzopyran derivative and its pharmaceutically acceptable salt according to claim 6, wherein the $R^3$ and $R^4$ in the formula (I) are combined with each other to represent an oxygen atom and the $R^5$ and $R^7$ are not combined with each other to represent a carbon-carbon bond.

10. A benzopyran derivative and its pharmaceutically acceptable salt according to claim 9, wherein $R^9$ in the formula (I) is a group represented by the formula:

wherein any one of $R^{11}$ and $R^{12}$ represent a $C_1$–$C_6$ lower alkyl group or $R^{11}$ and $R^{12}$ are combined with each other to form a $C_3$–$C_7$ carbon ring.

11. A benzopyran derivative and its pharmaceutically acceptable salt according to claim 6, wherein the $R^3$ and $R^4$ in the formula (I) are combined with each other to represent an oxygen atom and the $R^5$ and $R^7$ are combined with each other to represent a carbon-carbon bond.

12. A benzopyran derivative and its pharmaceutically acceptable salt according to claim 11, wherein $R^9$ in the formula (I) is a group represented by the formula:

wherein any one of $R^{11}$ and $R^{12}$ represent a $C_1$–$C_6$ lower alkyl group or $R^{11}$ and $R^{12}$ are combined with each other to form a $C_3$–$C_7$ carbon ring.

13. An ACAT inhibitor comprising as an active ingredient a benzopyran derivative or its pharmaceutically acceptable salt according to claim 1.

14. An anti-hyperlipidemia agent comprising as an active ingredient a benzopyran derivative or its pharmaceutically acceptable salt according to claim 1.

15. An anti-atherosclerosis agent comprising as an active ingredient a benzopyran derivative or its pharmaceutically acceptable salt according to claim 1.

* * * * *